United States Patent [19]

Novak

[11] Patent Number: 5,965,449
[45] Date of Patent: Oct. 12, 1999

[54] METHOD OF ASSESSING RISK FOR CARDIOVASCULAR DISEASE AND OTHER DISORDERS AND PHYTOSTEROL-BASED COMPOSITIONS USEFUL IN PREVENTING AND TREATING CARDIOVASCULAR DISEASE AND OTHER DISORDERS

[75] Inventor: Egon Novak, Richmond, Canada

[73] Assignee: Forbes Medi-Tech, Inc., Canada

[21] Appl. No.: 08/675,018

[22] Filed: Jul. 3, 1996

[51] Int. Cl.$^6$ .................................................. G01N 33/92
[52] U.S. Cl. ............................ 436/71; 436/63; 600/481; 600/483
[58] Field of Search .................... 436/8, 13, 63, 436/71; 128/668, 670; 600/481, 483

[56] References Cited

FOREIGN PATENT DOCUMENTS

96/10033  4/1996  WIPO .

OTHER PUBLICATIONS

Vuoristo et al. "Serum Plant Sterols and Aathosterol Related . . . in Coeliac Disease", *Clinica Chimica Acta,* vol. 174, 1988, pp. 213–224.

Ling et al. "Mini review—Dietary Phytosterols . . . " *Life Sciences,* vol. 57, No. 31, pp. 195–206, 1995.

Primary Examiner—Maureen M. Wallenhorst
Attorney, Agent, or Firm—Townsend and Townsend and Crew LLP

[57] ABSTRACT

Methods are provided for determining whether a subject animal has an increased risk of cardiovascular or related disorder. The level of serum campesterol and beta-sitosterol are determined and a campesterol/beta-sitosterol ratio obtained. The ratio determined for the subject animal is compared with that of a normal control animal and correlated with the risk of cardiovascular or a related disorder.

13 Claims, 8 Drawing Sheets

PRACTICAL GUIDELINES FOR CARDIOVASCULAR RISK (CVR) MANAGEMENT

CVR MARKER: PHYTOSTEROLS (PS)
CAMPESTEROL/β-SITOSTEROL RATIO (CSR)
TOTAL PHYTOSTEROLS (TP) TOTAL CHOLESTEROL (TC) INDEX
MATERIAL: SERUM
METHODS: GLS ANALYSIS

STEP I

INITIAL CVR ASSESSMENT

- HIGH TPS LOW TC (VEGETARIANS)
- HIGH TPS HIGH TC (LIPID METABOLIC DISORDERS)
- LOW TPS LOW TC DIABETES HYPOTHYROIDISM
- LOW TPS HIGH TC WESTERN DIET LIPID METABOLIC DISORDER HYPOTHYROIDISM

STEP II  FOLLOW-UP  DIETARY INTERVENTION

- HIGH TPS HIGH CSR TC (DIETARY COMPLIANCE)
- HIGH TPS, HIGH TC LOW CSR OR REVERSAL LABORATORY TESTS: LDL-C, HDL-C
- LOW TPS, LOW CSR OR REVERSAL LOW TP/TC INDEX OR REVERSAL LAB TESTS: TC; LDL-C; HDL-C; FBS; TSH; TG (DIABETES II, HYPOTHYROIDISM) HYPOTHROIDISM) DIETARY NON-COMPLIANCE

STEP III  FOLLOW-UP  THERAPEUTIC INTERVENTION RX: STATINS

STEP IV

THERAPEUTIC OBJECTIVES HIGH TPS; HIGH CSR; LOW TC; HIGH TPS/TC INDEX

THERAPEUTIC INTERVENTION RX: (TH, DIABETES) INCREASE PROTEIN SYNTHESIS

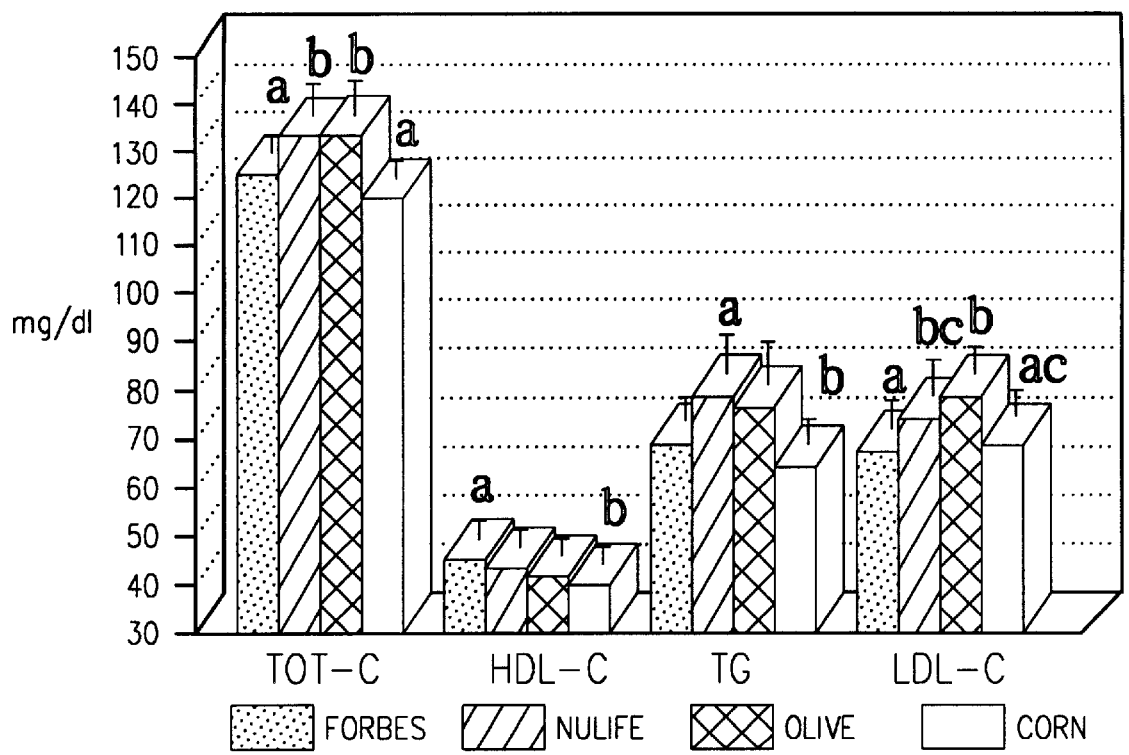
FIG. 1  PLASMA LIPID CONCENTRATION
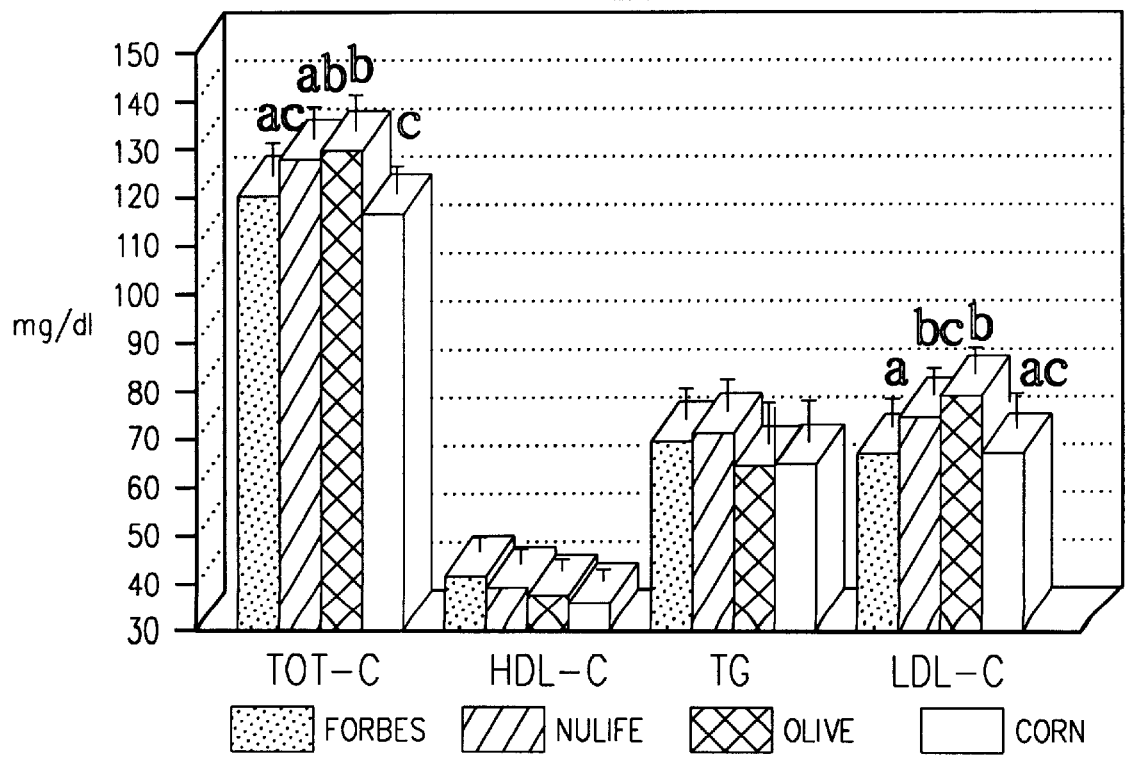
FIG. 2  PLASMA LIPID CONCENTRATION IN MALES

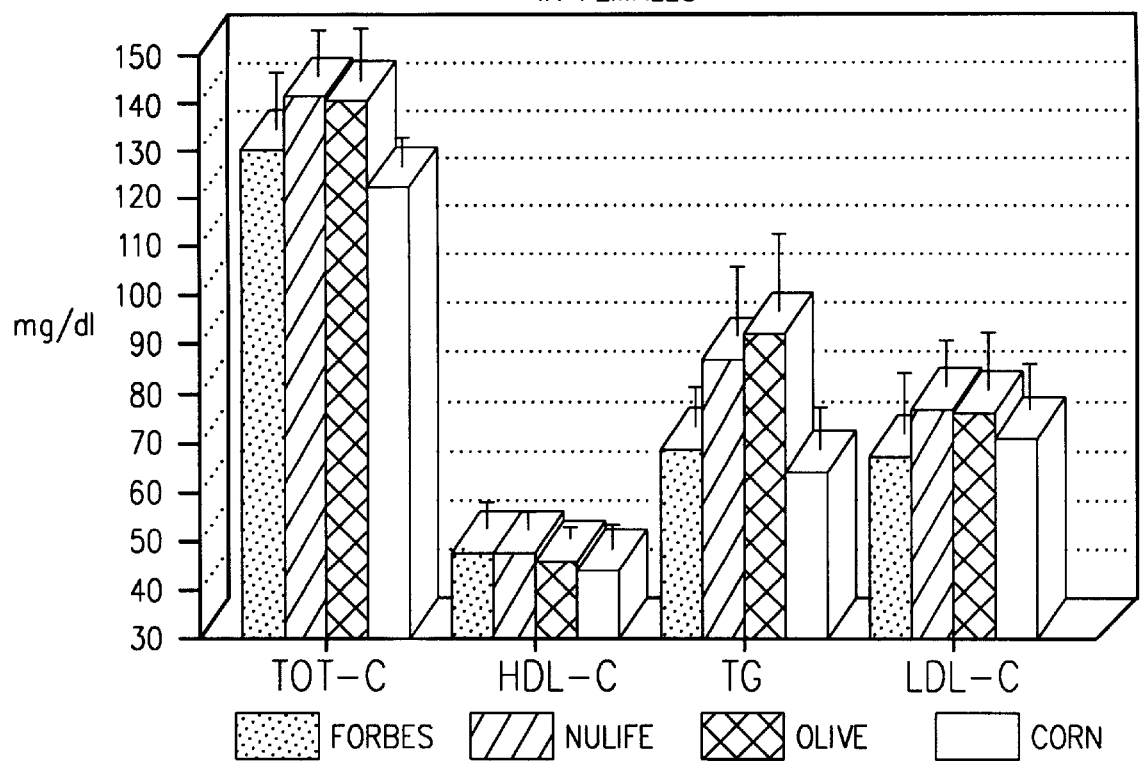
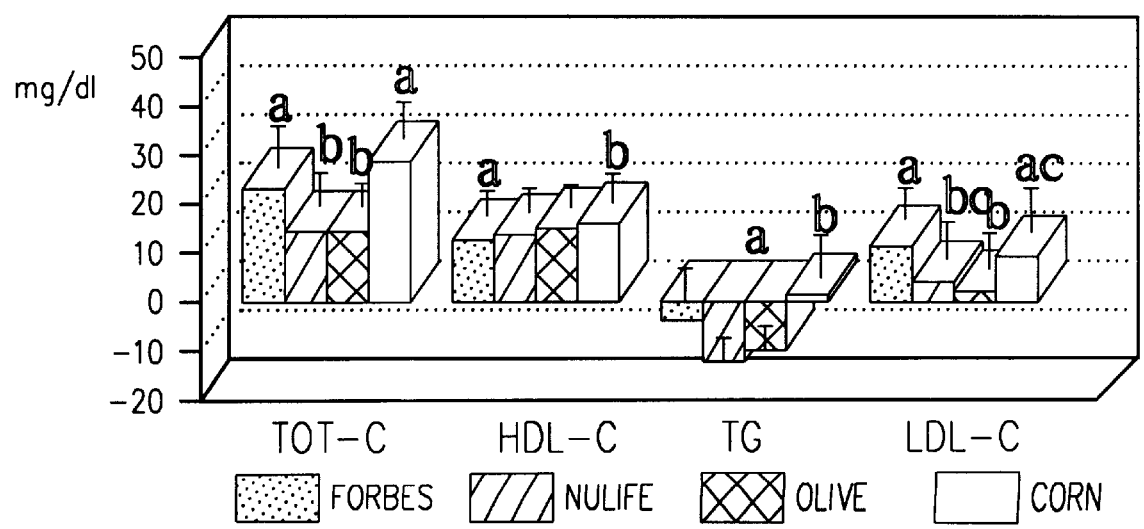

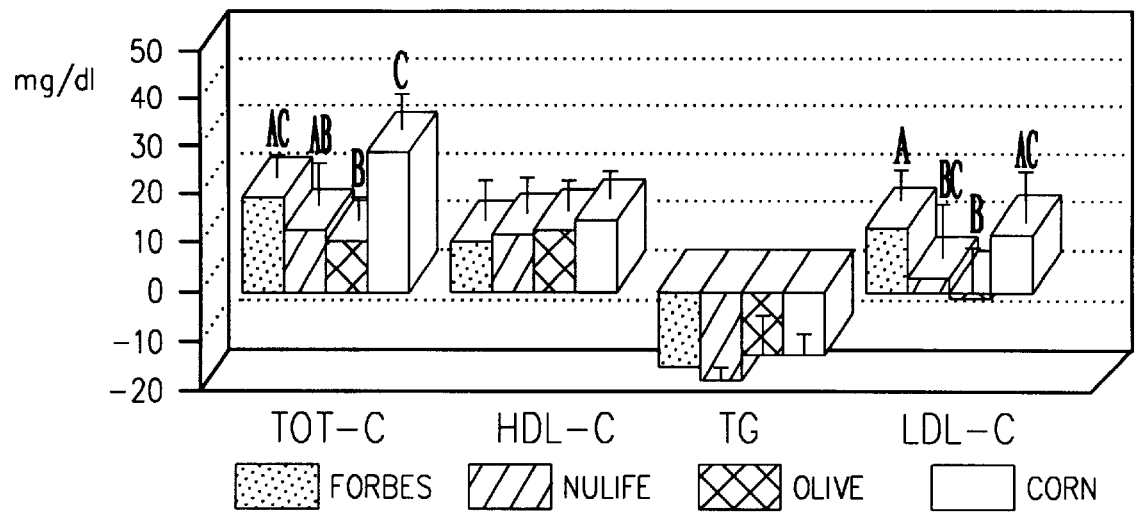
FIG. 5 PLASMA LIPIDS IN MALES
DECREASE RELATIVE TO BASELINE
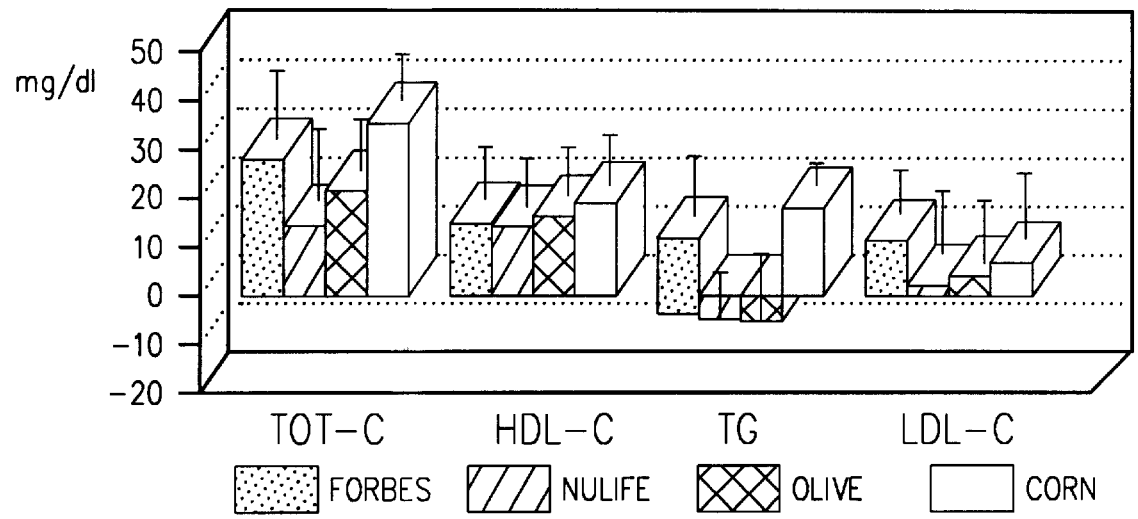
FIG. 6 PLASMA LIPIDS IN FEMALES
DECREASE RELATIVE TO BASELINE

PHYTOSTEROL CONCENTRATIONS IN BLOOD PLASMA
IN DIFFERENT TREATMENT GROUPS

EFFECT OF PHYTOSTEROLS ON ENTEROCYTE LIPOPROTEIN SHUTTLE (SIGMASTANOL EXCESS)

SL- Sigmastanol
MIE- Microemulsion
Apo- B-Apoprotein B
MTP- Microsomal Transfer Protein
VLDL- Very Low Density Lipoprotein
MAE- Macroemulsion

SYNTHESIS OF FREE CHOLESTEROL IN RED BLOOD CELL

METHOD OF ASSESSING RISK FOR CARDIOVASCULAR DISEASE AND OTHER DISORDERS AND PHYTOSTEROL-BASED COMPOSITIONS USEFUL IN PREVENTING AND TREATING CARDIOVASCULAR DISEASE AND OTHER DISORDERS

FIELD OF THE INVENTION

The present invention the physiological homeostasis of cholesterol using phytosterols and in particular to the use of phytosterols as independent risk markers or indicators of cardiovascular disease and other related disorders. The present invention also relates to the correction of deficiencies indicated by the results of these markers using phytosterol-based compositions.

BACKGROUND OF THE INVENTION

While recent advances in science and technology are helping to improve quality and add years to human lives, the prevention of atherosclerosis, the underlying cause of cardiovascular disease ("CVD"), has not been properly addressed and remains the leading cause of disability and death among middle-aged men. Cardiovascular disease is the leading contributor towards spiralling health care costs, estimated at approximately $17 billion in Canada and remains the most common single cause of death in both men and women. Each year, more than 1,000,000 coronary angiography procedures, approximately 400,000 angioplasties and 400,000 coronary artery bypass operations are performed in the United States alone. The 1992 statistics in Washington State indicate that CVD mortality accounts for 40% of all mortality with overall CVD death slightly more common in women than in men. By the age of 60, one in five men in the United States had experienced a coronary event compared to only one in 17 women. After the age of 60, death from coronary heart disease is one in four for both men and women.

Research to date suggests that cholesterol may play a primary role in atherosclerosis by forming a atherosclerotic plaques in blood vessels, ultimately cutting off blood supply to the heat muscle or alternatively to the brain or legs, depending on the location of the plaque in the arterial tree[1,2]. Recent overviews have indicated that a 1% reduction in a person's total serum cholesterol level yields a 2–3% reduction in risk of coronary artery disease[3]. Statistically, a 10% decrease in average serum cholesterol (e.g. from 6.0 mmol/L to 5.4 mmol/L) may result in the prevention of 100,000 deaths in the United States annually[4].

1. Law M. R., Wald N. J., Wu T., Hackshaw A., Bailey A.; Systemic underestimation of association between serum cholesterol concentration and ischemic heart disease in observational studies: Dam from BUPA Study; Br. Med. J.,1994; 308: 363–366.
2. Law M. R., Wald N. J., Thompson S. G.; By how much and how quickly does reduction in serum cholesterol concentration lower risk of ischemic heat disease?; Br. Med. J., 1994; 308: 367–373.
3. La Rosa J. C., Hunninghake D., Bush D., et al.; The cholesterol facts: a summary of the evidence relating dierary fats, serum cholesterol and coronary heart disease: a joint statement by the American Heart Association and the National Heart, Lung and Blood Institute. Circulation 1990; 81: 1721–33.
4. Havel R. J., Rapaport E.; Drug Therapy: Management of Primary Hyperlipidemia. New England Journal of Medicine, 1995; 332: 1491–1498.

Sterols are important cyclized triterpenoids that perform many critical functions in cells. Phytosterols such as campesterol, stigmasterol and beta-sitosterol in plants, ergosterol in fungi and cholesterol in animals are each primary components of the cellular and sub-cellular membranes in their respective cell types. The dietary source of phytosterols in humans comes from vegetables and plant oils. The estimated daily phytosterol content in the conventional western-type diet is approximately 250 milligrams in contrast to a vegetable diet which would provide double that amount.

Although having no nutritional value to humans, phytosterols have recently received a great deal of attention due to their possible anti-cancer properties and their ability to decrease cholesterol levels when fed to a number of mammalian species, including humans. Phytosterols aid in limiting cholesterol absorption[5], enhance biliary cholesterol excretion[6] and shift cholesterol from atherosclerotic plaque[7]. While many of the mechanisms of action remain unknown, the relationship between cholesterol and phytosterols is apparent. This is perhaps not surprising given that chemically, phytosterols closely resemble cholesterol in structure. The major phytosterols are beta-sitosterol, campesterol and stigmasterol. Others include stigmastanol (beta-sitostanol), sitostanol, desmosterol, chalinasterol, poriferasterol, clionasterol and brassicasterol.

5. Gould R. G., Jones R. J., LeRoyu G. V., Wissler R. W., Taylor C. B.; Absorbability of B-sitosterol in humans; Metabolism, (August) 1969; 18(8): 652–662.
6. Tabata T., Tanaka M., Lio T.; Hypocholesterolemic activity of phytosterol. II (author's transl.); Yakugaku Zasshi, 1980; 100(5): 546–552.
7. Hepistall R. H., Porter K. A.; The effect of B-sitosterol on cholesterol-induced atheroma in rabbits with high blood pressure; Br. J. Experimental Pathology, 1957; 38: 49–54.

While there is data indicating that one of the major risk factors for atherosclerosis or CVD is the level of blood cholesterol, this risk factor cannot be considered conclusive. It has been found that individuals having serum cholesterol levels within the normal, acceptable range may still be at risk- and do develop atherosclerosis and CVD. For this reason, a more reliable risk factor or indicator is required.

It is an object of the present invention to obviate or mitigate the above disadvantages and limitations regarding CVD risk assessment, treatment and dietary monitoring for those at risk for CVD.

SUMMARY OF THE INVENTION

The present invention provides a set of protocol variables for assessing risk for cardiovascular disease ("CVD"), lipid and thyroid disorders and diabetes in an animal which is independent of the cholesterol level in the animal and provides phytosterol compositions useful for correcting physiological imbalances in cholesterol homeostasis indicated by the results of the protocol variables.

In particular, the present invention provides a method of determining in an animal the level of total plasma campesterol and the ratio of serum campesterol to the level of beta-sitosterol comprising the steps of taking a serum sample, determining the campesterol level therein, determining the beta-sitosterol level therein, dividing the campesterol level by the beta-sitosterol level to form a campesterol/beta-sitosterol ratio and comparing the campesterol level and the campesterol/beta-sitosterol ratio with that of a normal control, wherein the improvement comprises selecting the campesterol level and the campesterol/beta-sitosterol ratio as indicators or markers and correlating the level and ratio to the risk in the animal of CVD and other disorders.

Further, the present invention defines a method of assessing risk in an animal for CVD, lipid and thyroid disorders and diabetes which comprises determining in the animal the ratio of serum campesterol to beta-sitosterol, determining in the animal the level of serum total phytosterol, determining in the animal the level of serum total cholesterol and comparing the ratio and the two levels so obtained to the respective levels and ratio in a normal control animal.

Further, the present invention provides a method of enhancing in an animal the inhibitory effect of phytosterols on cholesterol enterocyte absorption which comprises administering to the animal a composition comprising one or more phytosterols which inhibit predominantly cholesterol and beta-sitosterol absorption.

Further, the present invention provides a composition for enhancing in an animal the inhibitory effect of phytosterols on cholesterol enterocyte absorption which comprises one or more phytosterols which inhibit predominantly cholesterol and beta-sitosterol absorption.

The present invention, defined broadly above, includes two principal features. The first involves the various CVD risk markers which together form protocol variables. The second involves the enhancement of the modulatory effect of phytosterols on plasma cholesterol levels in animals, which effect is used beneficially to correct imbalances in cholesterol homeostasis using phytosterol compositions.

With respect to the first feature, the key to the protocol and markers used within the scope of the present invention is that they may be viewed independently of the level of cholesterol in the animal. This it in direct contrast to the current art and teachings regarding the assessment of CVD. According to the protocol of the present invention, the serum campesterol/beta-sitosterol ratio of an individual, taken alone or in combination with one or all of the:

(1) total serum phytosterol level;

(2) total phytosterol-cholesterol ratio; and (3) campesterol/Apo-protein B cholesterol ratio provides critical information on the health of that individual. As will be explained further hereinbelow, these indicators or markers may be used by medical personnel to assess risk for CVD, lipid and thyroid disorders and diabetes. Generally, it has been found that there is a positive correlation between the serum campesterol level (and campesterol/B-sitosterol ratio of 1.0 or above) and a favourable cholesterol profile (a decreases in total and high density lipoprotein cholesterol) and a positive correlation between the serum B-sitosterol level (and ratio of below 1.0) and a poor cholesterol profile (an increase in total and low density lipoprotein cholesterol).

Equally importantly, the markers of the present invention may be used to assess compliance of an individual to special diets, for example, low cholesterol diets or diets in which phytosterol levels are to be enhanced. Using the results of the protocol, a treatment regime may be developed specifically to target the particular deficiency on that individual.

With the exception of the optional assessment of the total phytosterol/cholesterol ratio, each of the indicators described herein is independent of the serum cholesterol level, the latter of which, as described above, may be an unreliable CVD risk factor. Accordingly, using the protocol of the present invention, and particularly the serum campesterol and campesterol/B-sitosterol ratio, a predisposition to CVD or other disorders may be discovered and appropriately treated despite a testing in that individual of a normal or acceptable serum cholesterol level.

BRIEF DESCRIPTION OF THE DRAWINGS

The present invention is illustrated by way of the following non-limiting drawings in which:

FIG. 1 is a graph representing showing the plasma lipid concentrations of total cholesterol, high density lipoprotein cholesterol, triglycerides and low density lipoprotein in healthy male and female subjects consuming either the composition of the present invention or other comparative diets;

FIG. 2 is a graph representing the plasma lipid concentrations of total cholesterol, high density, lipoprotein cholesterol, triglycerides and low density lipoprotein cholesterol in healthy male subjects consuming either the composition of the present invention or the comparative diets;

FIG. 3 is a graph representing the plasma lipid concentrations of total cholesterol, high density lipoprotein cholesterol, triglycerides and low density lipoprotein cholesterol in healthy female subjects consuming either the composition of the present invention or a comparative diet;

FIG. 4 is a graph representing the decrease in plasma lipid concentrations of total cholesterol, high density lipoprotein cholesterol, triglycerides and low density lipoprotein cholesterol in healthy male and female subjects consuming either the composition of the present invention or a comparative diet;

FIG. 5 is a graph representing the decrease in plasma lipid concentrations of total cholesterol, high density lipoprotein cholesterol, triglycerides and low density lipoprotein cholesterol in healthy male subjects consuming either the composition of the present invention or a comparative diet;

FIG. 6 is a graph representing the decrease in plasma lipid concentrations of total cholesterol, high density lipoprotein cholesterol, triglycerides and low density lipoprotein cholesterol in healthy female subjects consuming either the composition of the present invention or a comparative diet;

PREFERRED EMBODIMENTS OF THE INVENTION

Figure 7:
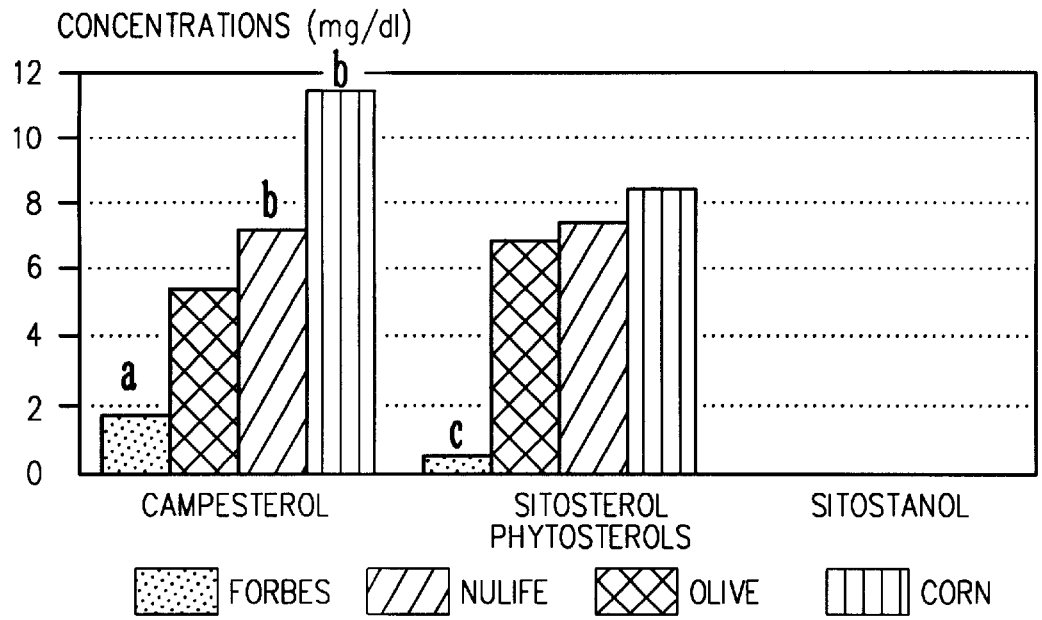
FIG. 7 is a graph showing phytosterol concentrations in blood plasma in various treatment groups including the group administered the composition of the present invention and in particular showing the relative concentrations of campesterol, sitosterol and sitostanol.

The "protocol" of the present invention refers to the analysis of the serum campesterol/beta-sitosterol ratio of an individual alone or in combination with one or all of the following:

(1) the total serum phytosterol level;

(2) the total phytosterol-cholesterol ratio;

(3) the campesterol/Apo-protein B cholesterol ratio.

In order to understand the nature of these ratios and levels and to appreciate the value of the information they provide to medical personnel, it is necessary to outline some aspects of the interplay of cholesterol and phytosterol transport mechanisms, absorption, excretion and tissue distribution.

The intestine and liver are the primary organs of cholesterol homeostasis, the absorption of dietary cholesterol and the synthesis and excretion of cholesterol.

The absorption of dietary cholesterol begins with the absorption of lipids from the intestine, Cholesterol and fatty acids are then esterified in mucosal cells to form non-polar products and arranged with apoproteins to form chylomicrons. Chylomicrons enter the general circulation via the lymphatic system and are hydrolysed by plasma lipoprotein lipase into free fatty acids and monoglycerides. The dietary cholesterol transported in chylomicrons is delivered almost entirely to the liver as part of a chylomicron remnant which is then processed by hepatocyte cholesterol-7 alpha-hydroxylase into bile acids or excreted unmetabolized. Conversely, phytosterols are not endogenously synthesized in the body, therefore, are derived solely from the diet (originating from plants and edible oils) entering the body only via intestinal absorption. Within the intestine, cholesterol absorption is preferred over phytosterol absorption in mammals. For healthy humans, the absorption rate of phytosterols is usually less than 5% of dietary levels which is considerably lower than that of cholesterol which is over 40%[8,9]. Thus, approximately 95% of dietary phytosterols enter the colon. Only 0.3 to 1.7 mg/dl of phytosterols are found in human serum under normal conditions compared with daily dietary intakes of 160 to 360 mg/day but plasma levels have been shown to increase up to twofold by dietary supplementation[10,11,12]. In summary, phytosterol serum levels are low due to poor phytosterol absorption and rapid elimination within the intestine. The exact mechanisms responsible for slow phytosterol intestinal absorption are not known. What is known and well documented, however, is that phytosterols aid in limiting intestinal cholesterol absorption[13], enhance biliary cholesterol excretions[14], shift cholesterol from atherosclerotic plaque[15] and prevent liver steatosis[16]. The level of total serum cholesterol is a result of opposing metabolic forces including synthesis, absorption, elimination and tissue distribution along with some limiting effects of intestinal phytosterols on cholesterol absorption.

8. G. Salen et al., J. Lipid Res 30 1319–1330 (1989).
9. C. Sylven, Biochim. Biophya. Acta 203 365–375 (1970).
10. Supra, at 8.
11. Supra, at 9.
12. G. Salen et al., J. Clin. Invest. 49 952–967 (1970).
13. Supra, at 5.
14. Supra, at 6.
15. Supra, at 7.
16. Jones P. J. H., Ling W. H.; Enhanced efficacy of sitostanol-containing versus sitostanol-free phytosterol mixtures in altering lipoprotein cholesterol levels and synthesis in rats; Atherosclerosis, January 1996 (accepted for publication).

Figure 11:
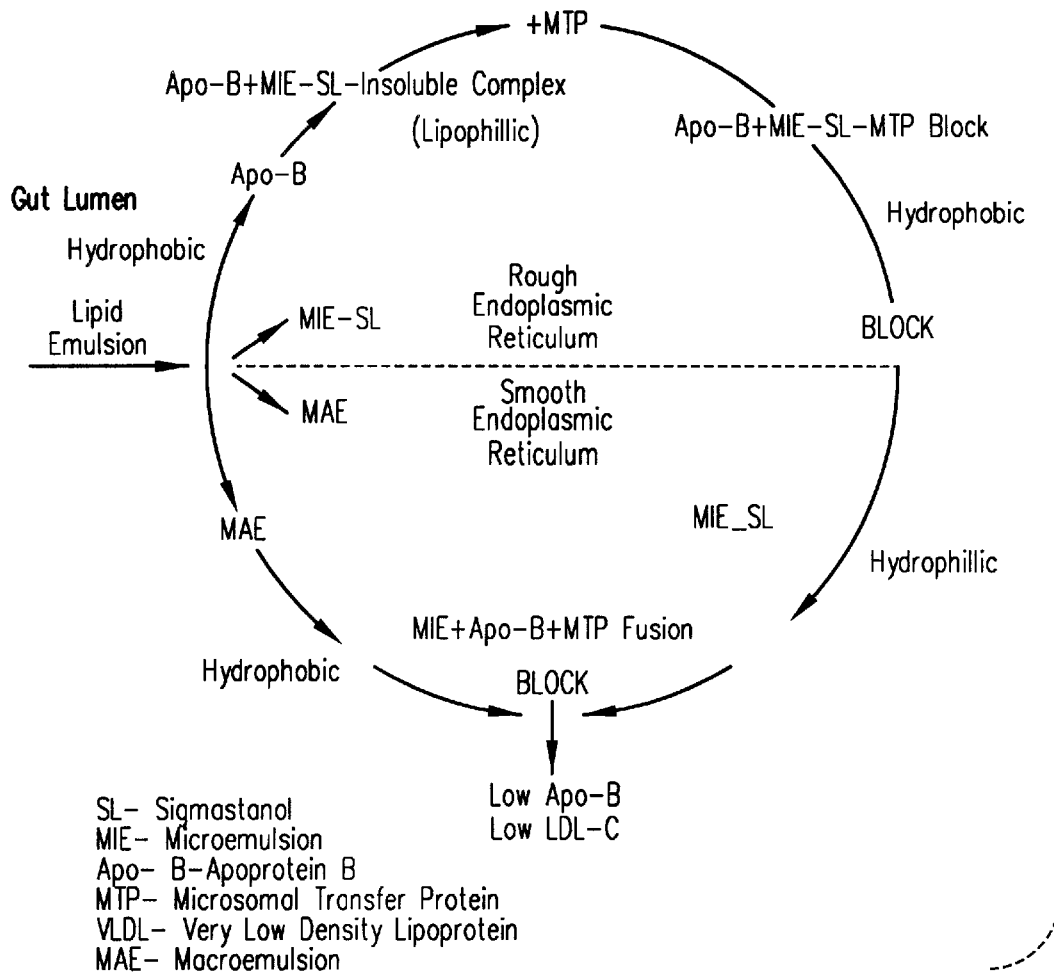
FIG. 11 is a schematic depicting the enterocyte shuttle mechanism described herein.

As described herein, the "extrinsic effect" refers to the role of phytosterols in the inhibition of cholesterol absorption by the enterocytes. One aspect of the mechanism behind the protocol of the present invention involves the existence of an independent extrinsic effect wherein individual phytosterols compete between themselves and cholesterol for the enterocyte shuttle transport from the gut lumen to the lymph. In other words, each plant sterol has a different effect on cholesterol absorption. There are several aspects to consider in intestinal cholesterol absorption, in particular, bioavailability, membrane transport and enterocyte intracellular transfer. Within the present invention, it has been found that phytosterol inhibition of the enterocyte cholesterol shuttle is based on the assumption that cholesterol transport across cells from the gut lumen to lymph or plasma requires intracellular re-assemblance of cholesterol rich microparticle complexes with Apoprotein-B as shown in FIG. 11. In the enterocyte, phytosterols compete with cholesterol for Apoprotein-B, forming more lipophilic, apolar Apoprotein-B complexes which cause shuttle inhibition and decrease lymphatic cholesterol content. Depending on the type of phytosterol and as described further below, solubility and shuttle inhibition can be transient and reversible (campesterol, beta-sitosterol) or permanent and irreversible (sitostanol). The proposed effect of phytosterols on the enterocyte lipoprotein shuttles is shown in FIG. 11.

The common phytosterol molecular structure resembles cholesterol and depending on the phytosterol composition and favourable intestinal phytosterol/cholesterol dietary ratio, phytosterol can significantly alter cholesterol absorbtion. Alternatively, due to a decrease or absence of cellular synthesis of Apoprotein-B, both serum phytosterol and cholesterol levels are low (i.e. Diabetes Type II, Abetalipoproteinemia, and Hypothyroidism). The changes in enterocyte shuttle selectivity, presumably due to an Apo-B mutation, could lead to high phytosterol and cholesterol serum levels, with campesterol intestinal absorbtion declining, causing a decrease in the campesterol/B-sitosterol ratio (primary familial hypercholesterolemia and sitosterolemia).

The competition between individual phytosterols such as campesterol, beta-sitosterol and sitostanol and cholesterol for intestnal absorption is of importance in that there is a definite association between high cholesterol serum levels and cardiovascular morbidity and mortality. Intestinal cholesterol absorption varies between 35% to 57% and for a specific .sterol this absorption is generally as follows: campestanol-12.5%; campesterol-9.6%, sigmastanol-9.6%, beta-sitosterol-4.2%, and 0% for sitostanol. The enterocyte shuttle transport has been found to be dependent on Apoprotein-B, which has a high cholesterol affinity but low specificity. Accordingly, depending on the particular phytosterol composition provided to an individual, the phytosterol (extrinsic effect) can significantly alter cholesterol absorption. This effect is dependent on the specificity and selectivity of the cholesterol enterocyte shuttle and varies according to genetic and hormonal influences. For example, patients with abetalipoproteinemia do not absorb cholesterol, have low plasma cholesterol levels, and do not get atherosclerosis. Conversely, in sitosterolemia, a rare genetic disorder, high plasma phytosterol levels and high plasma Apoprotein-B levels lead to premature atherosclerosis.

Knowing that the enterocyte absorption mechanism is dependent on Apoprotein-B shuttle and that phytosterols compete between themselves and with cholesterol for Apoprotein-B, it is then possible to tailor the particular phytosterol composition to be administered to an individual in order to achieve the desired "competition" at the shuttle to regulate cholesterol absorption. By modifying the dietary campesterol/B-sitosterol ratio, the physiological compositions of the present invention correct lipid metabolic disorders and compensate for high risk diets.

Although sitostanol has an efficient blocking effect, it is not physiologically beneficial to administer a pure highly hydrophobic sitostanol composition as the enterocyte shuttle binding is permanent and irreversible with this particular phytosterol. Both campesterol (which is hydrophilic) and beta-sitosterol (which is more neutral) reversibly bind to Apoprotein-B and compete at the enterocyte shuttle as described above.

In addition, it has been found that determining the serum campesterol and serum Apoprotein-B levels provides to the clinician critical information as to the functioning of the enterocyte shuttle in an individual.

Assessing the Apoprotein-B level in accordance with the present invention provides a diagnosis of lipid and thyroid disorders as well as diabetes. For example, due to a decrease or absence of cellular synthesis of Apoprotein-B, both serum phytosterol and cholesterol levels are low, which may be indicative of Diabetes Type II, abetalipoproteinemia, or hypothyroidism. Any changes in shuttle Selectivity, presumably due to Apoprotein-B mutations, could lead to high phytosterol and cholesterol serum levels, with campesterol intestinal absorption declining causing a decrease in the campesterol/beta-sitosterol ratio. This would be indicative of primary familial hypercholesterolemia or sitosterolemia.

As described herein, the "intrinsic effect" comprises phytosterol effects on cholesterol and bile acid synthesis, enterocyte and biliary cholesterol excretion, bile acid excretion, changes in enzyme kinetics and cholesterol transport between various compartments:

(i) primary compartments:
  (a) liver, enterocyte
  (b) body fat (lipocyte), (cholesterol metabolic transformation, energy stores)
(ii) secondary compartments:
  (a) body organs, tissues, cells (active cholesterol recipients)
(iii) tertiary compartments:
  (a) endothelial cells, monocytes, atherosclerotic plaque (overflow, passive cholesterol recipient)

As in the enterocyte shuttle, phytosterols compete with cholesterol in the hepatic cells of the liver for elimination. In contrast to the enterocyte shuttle, however, the elimination of phytosterols via the bile route is faster than cholesterol with a three-fold bile sitosterol enrichment relative to cholesterol[17]. Correspondingly, the endogenous phytosterol pool size is low compared to cholesterol due to the combination of poor phytosterol intestinal absorption and faster biliary excretion.

17. Salen G., Ahrens Jr. E. H., Grundy S. M.; The metabolism of B-sitosterol in man; J. Clin. Invest., 1970; 49: 952–967.

It has been found within the scope of the present invention that the serum campesterol/beta-sitosterol ratio in an individual correlates positively with this intrinsic phytosterol effect. Practically, what this means is that CVD and other disorders may be detected using this level and ratio and irrespective of the serum cholesterol level. An individual may haste an acceptable serum cholesterol level but may have a low serum campesterol level or a beta-sitosterol level in excess of the serum campesterol level (a low ratio) indicating that this individual may be at risk for CVD and that follow-up tests and therapeutic intervention may be required.

In essence, a high serum campesterol and a high campesterol/beta-sitosterol ratio indicates the operation of a healthy enterocyte shuttle in an individual. Phytosterols are being rapidly excreted through the biliary route and are thereby readily available in greater concentrations to compete with cholesterol at the intestinal enterocyte level. It has been found that the level of serum phytosterols, particularly hydrophillic and most particularly campesterol best reflects the efficacy of this effect.

Thus, in one act of the present invention, the ratio of serum campesterol and serum beta-sitosterol in an individual is compared to that of a normal control in order to correlate the risk of that individual having CVD or other diseases. The ratio in the normal control is preferably not less than 0.75 and most preferably is between 1.0 and 1.5. Ratios in this range, wherein campesterol is close to even or in excess of beta-sitosterol reflect and efficiently working "enterocyte shuttle". Ratios below 0.75 are generally indicative of an abnormality or imbalance in the enterocyte shuttle. It is likely that phytosterols are protecting the shuttle from cholesterol overload by the cumulative effects of the enterohepatic phytosterol circulation ("campesterol effect").

Although the level of serum campesterol and campesterol/beta-sitosterol ratio of an individual compared to that of a normal control provides valuable information as to the general health and diet of the individual in question, this information can also be taken in conjunction with other biological variables as compared to normal control levels or ratios to form a set of "protocol" variables for risk assessment. These variables may include one or more of the following:

(1) total serum phytosterol level;
(2) total serum cholesterol level;
(3) total phytosterol/cholesterol ratio; and
(4) campesterol/Apoprotein-B cholesterol ratio.

This serum analysis includes assessments of both the "extrinsic" and "intrinsic" biological effects as follows:

SERUM PHYTOSTEROL ANALYSIS

| | | DIET | |
|---|---|---|---|
| VARIABLE | EFFECT | VEGETARIAN | CARNIVOROUS |
| Campesterol:Beta-sitosterol ratio | Extrinsic Intrinsic | High | Low |
| Total Phytosterol:Total Cholesterol Ratio | Coeffect | High | Low |
| Campesterol:Apo-B Cholesterol Ratio | Extrinsic | High | Low |
| Campesteral Serum Levels | Intrinsic | High | Low |
| Total Plant Sterol Serum Levels | Coeffect | High | Low |

A comparison of these protocol variables in vegetarian diets (high in phytosterols) as compared to carnivorous diets (generally low phytosterols) is also shown.

Preferably, the level of serum total cholesterol in a normal control is not more than 5.2 mmole/L. Preferably, the level of serum total phytosterol in a normal control is from about 2.0 to 6.0 $\mu$mole/L. Preferably, the campesterol/Apoprotein-B cholesterol ratio is greater than 0.5 in the normal control.

The protocol of the present invention enables medical personnel to assess those individuals who may be at risk for CVD and other disorders by the use of modifiable protocol variables. For example, it may be shown that:

(i) an alteration in phytosterol shuttle selectivity can lead to a low plasma campesterol/beta-sitosterol ratio or to its reversal;
(ii) low fractional phytosterol serum levels may be due to low dietary phytosterol content or to a down-regulation of the enterocyte shuttle; and
(iii) up-regulation of the enterocyte shuttle results in high plasma, cholesterol and fractional phytosterol levels and/or reversal of campesterol/beta-sitosterol ratio.

The protocol variables provide valuable information on diet, diet and medication adherence and the existence of underlying lipid disorders, diabetes and thyroid disorders, as a method for monitoring and evaluating the treatment process for CVD.

Figure 12:
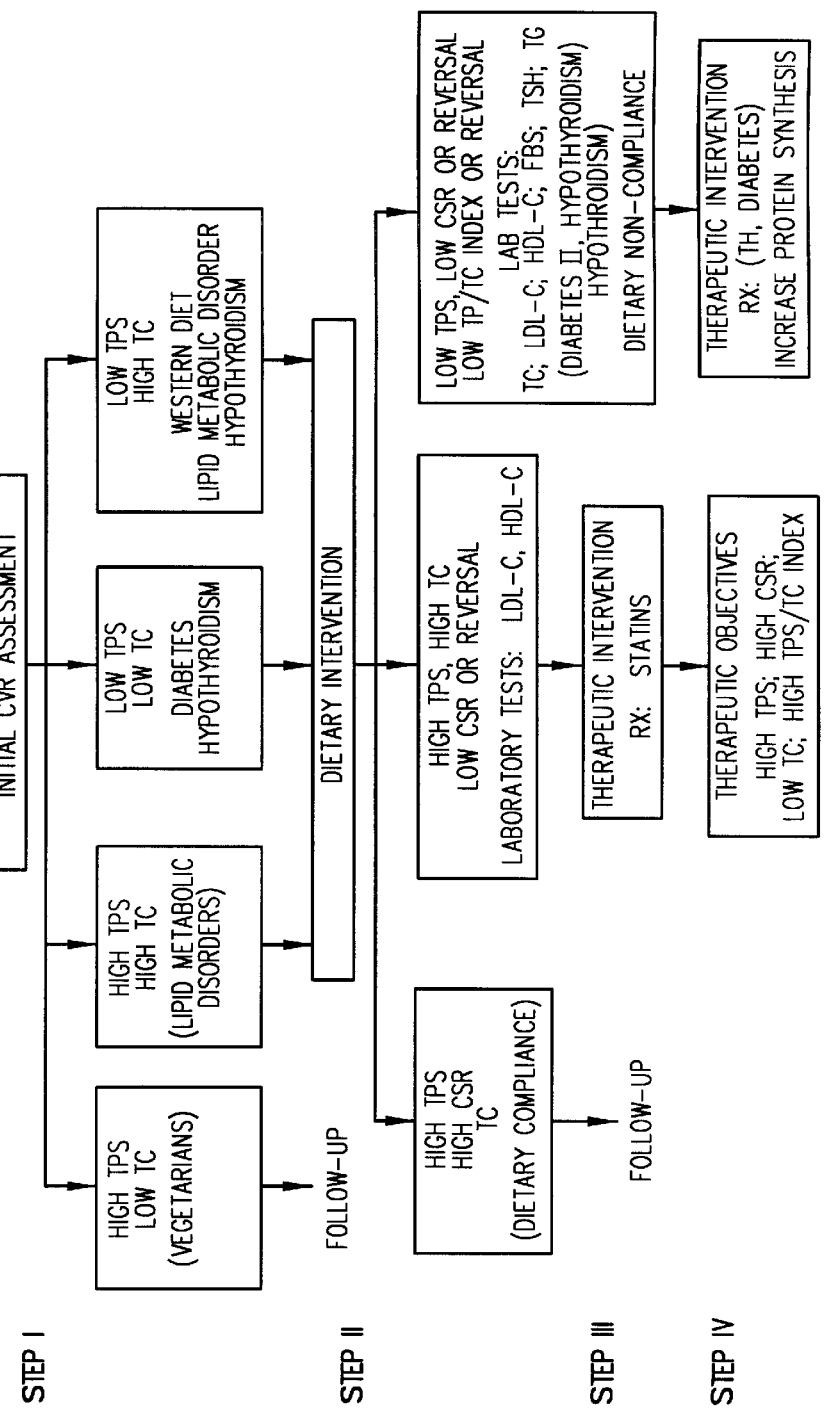
FIG. 12 is a schematic depicting, in stages, the protocol variables of the present invention.

In a most preferred form of the present invention and with reference to FIG. 12, the protocol variables may be applied in determining risk for CVD and other disorders as follows:

Step I comprises an initial assessment including a determination of serum total phytosterols ("TPS") and total serum cholesterol ("TC") in the individual and a comparison of these levels to normal control levels. Generally, an individual having a high TPS and a low TC compared to a normal control requires no therapeutic or dietary intervention. It is likely that this type of individual consumes a vegetarian diet. An individual having a high TPS and a high TC should be assessed further for lipid metabolic disorders such as sitosterolemia. It is at step II that the results of the serum campesterol/beta-sitosterol ("CSR") are critical. An individual having a high TPS as compared to a normal control and a high CSR, regardless of the TC level is healthy and is complying with imposed diet restrictions. The fact that the CSR supplants the serum TC level as a critical indicator of disease is fundamental in appreciating the value of the present invention and its applications to medical diagnostics and treatment.

An individual having a high TPS, high TC and a low CSR or reversal of this ratio is at risk of CVD and should be treated accordingly. This treatment may involve dietary intervention using the phytosterol composition of the present invention alone or in combination with other therapeutic intervention. The goal of the treatment protocol is to increase TPS, decrease TC (thereby increasing the TPS/TC ratio to 1.0 or greater) and increase CSR. Many of these objectives may be achieved by the administration of the phytosterol composition as described hereinbelow.

An individual having a low TPS, a low CSR (or reversal), a low TPS/TC ratio (less than 1.0 or reversal) is at risk of or has a thyroid disorder or diabetes requiring therapeutic intervention. Alternatively, this type of protocol result is indicative of dietary non-compliance i.e. the dietary plant sterile concentration is insufficient to maintain the required phytosterol/cholesterol homeostasis.

The present invention involves the determination and use of protocol variables in assessing risk for CVD and other related metabolic and lipid disorders. At the core of these variables is the serum campesterol/beta-sitosterol ratio or CSR which has been found to reflect both the selectivity and "efficacy" of the phytosterol shuttle. Ratios greater than 1.0 and most preferably at or near 1.5 are indicative of a healthy phytosterol/cholesterol homeostasis. In other words, the excretion of phytosterols through the hepatic biliary system is at an optimal level to compete with cholesterol at the enterocyte shuttle as described above, The balance of this competition is reflected in the favourable CSR. Conversely, a CSR below 1.0 and in particular below 0.75 (a CSR reversal) are clear indicators of CVD or other disorders (diabetes, hypothyroidism) regardless of the serum total cholesterol level in the tested individual.

Based on the results of the protocol variables, which reflect the modulatory effects of phytosterol on cholesterol metabolism, there is provided herein a new classification of cholesterol metabolic disorders as follows:
 (i) extrinsic effect disorder
   (a) decrease of cholesterol absorption
     high vegetable diet
     diet high in vegetable oils
     hypothyroidism
     diabetes mellitus type II
     abetalipoproteinemia
   (b) increase of cholesterol absorption
     high fat/high cholesterol diet
     primary familial hypercholesterolemia
     sitosterolemia
 (ii) intrinsic effect disorder
     diabetes mellitus type II
     hypothyroidism
     familial combined hyperlipidemia
     nephrotic syndrome Sitosterolemia is a rare inherited lipid storage disease, characterized chemically by elevated phytosterol plasma concentrations, normal cholesterol levels is and elevated low density lipoprotein cholesterol and Apoprotein-B[18]. This disease is associated with accelerated atherosclerosis. The primary defect appears to be increased phytosterol absorption along with an impairment of cholesterol and phytosterol bile secretion. Since an increase in cholesterol absorption occurs in spite of the high phytosterol plasma concentrations, it is likely that there is a failure of the down-regulation of the enterocyte shuttle by phytosterols. It has been found within the scope of the present invention that an indicator of sitosterolemia is the reversal of the campesterol/beta sitosterol ratio. This suggests a loss of phytosterol shuttle discrimination with serum or plasma accumulation of phytosterols and alpha-stanols. Normally, high serum phytosterol levels up-regulate cholesterol synthesis but cholesterol synthesis in sitosterolemic subjects is low, however, and low density lipoprotein-C turnover is increased. The inherited defect in sitosterolemia is thought to involve an abnormality of the HMG-CoA reductase gene. It may also be due to the inhibitory effect of high serum sitostanol on hepatic plant sterols and cholesterol excretion.

18. Bhatracharyya A., Conner W. E., B-Sitosterolemia and xanthomatosis. A newly described lipid storage disease in two sisters; J. Clin. Invest., 1974; 53: 1033–1043.

In Type II Diabetic patients, plasma phytosterol levels are low and inversely correlated to plasma insulin levels and it has been found within the scope of the present invention that the average campesterol/beta-sitosterol ratio is similar in diabetic and control groups with an excess of campesterol.

PHYTOSTEROL COMPOSITIONS

Phytosterols are widely available in vegetable oils, however, with the possible exception of floe bran oil, the phytosterol content of vegetable oils is not sufficient to significantly alter cholesterol intestinal absorption due to the low in intestinal dietary phytosterol/cholesterol ratio. In addition, vegetable oils vary in phytosterol content and composition. The main dietary oils phytosterol constituent, beta-sitosterol, decreases both total and low density lipoprotein-C (LDL-C) but alone is not very effective in modulating cholesterol homeostasis. The vegetable oils low in phytosterols such as coconut oil and olive oil and safflower oil are adequate, for maintaining cholesterol homeostasis in individuals with high dietary intake of vegetables i.e. for pure vegetarians but are inadequate without phytosterol supplementation for the balance and majority of the population. What is provided within this aspect of the present invention is a phytosterol composition which may be incorporated directly into food supplements, oils and vitamin and therapeutic formulations for treatment of CVD and for correcting dietary and other deficiencies indicated by the protocol variables as described aspect, it is contemplated that the compositions of the present invention be added as a standard food supplement (i.e. to vegetable oils) in a "high-risk population" or via a wholesale population administration approach. Alternatively, in other aspects, the compositions may be provided in primary, secondary or tertiary prevention treatment programs.

The phytosterol compositions of the present invention have exhibited a marked ability to achieve the therapeutic objectives indicated by the results of the protocol variables. In particular, the compositions of the present invention increase TPS, lower the serum TC and LDL-C and concomitantly increase the serum high density lipoprotein-C (HDL-C) and HDL-C/LDL-C ratio.

The compositions of the present invention comprise B-sitosterol, campesterol, stigmastanol (B-sitostanol) and optionally, campestanol. These compositions and the relative concentrations therein of the plant sterols are distinct from the known phytosterol compositions in many resects. Generally, in the compositions of the present invention, the relative concentration of B-sitosterol is lower than in the known compositions. Similarly, the relative concentration of sitostanol is higher within the scope of the present invention. Nonetheless, it is believed that it is the combination of the relative concentrations of the plant sterols and the particular types of plant sterols that have proved so beneficial in achieving the desired therapeutic objectives. In particular, if the concentration of sitostanol within the composition is insufficient, the efficacy as a therapeutic agent will be compromised.

In one embodiment, the composition of the present invention comprises at least 10% campesterol and no more than 75% B-sitosterol. In a more preferred form, the composition comprises from 10–25% campesterol, 10–25% stigmastanol and from 45–75% B-sitosterol. Optionally, the composition comprises from 2–6% campestanol, most preferably 3%.

It is to be understood, however, that other phytosterols may be added to the compositions of the present invention in order to enhance the therapeutic effect.

In another preferred form, the compositions of the present invention comprise the following ratio of phytosterols: beta-sitosterol (1); campesterol (0.2–0.4) and stigmastanol (0.2–0.5). More preferably, campesterol and stigmastanol together represent at least 50% of the total concentration of beta-sitosterol. In a most preferred form, the compositions of the present invention comprise the following ratio of phytosterols as compared to soybean-derived phytosterols:

Ratio of Known Phytosterols

|  | Approximate Purity (%) | B-sitosterol | Campesterol | Stigmastanol |
| --- | --- | --- | --- | --- |
| Soybean |  | 1 | 0.640 | 0.005 |
| Forbes-1 | 91.0 | 1 | 0.354 | 0.414 |
| Forbes-2 | 77.0 | 1 | 0.330 | 0.203 |
| Forbes-3 | 90.0 | 1 | 0.268 | 0.299 |

The composition and purity of two other extracts within the scope of the present invention are as follows:

|  |  | Composition (%) | | |
| --- | --- | --- | --- | --- |
|  | Approximate Purity (%) | B-sitosterol | Campesterol | Stigmastanol |
| Forbes-4 | 99.0 | 62.6 | 16.6 | 23.2 |
| Forbes-5 | 98.3 | 64.7 | 16.4 | 17.2 |

The most preferred composition of the present invention, based on column separations with fractionation of different fractions and their TLC, GC, GC-MS investigations, comprises the following fractions:

| Compounds | | |
| --- | --- | --- |
| Phytosterols | Campesterol - | 13.6% |
|  | Campestanol - | 3.4% |
|  | B-sitosterol - | 60.4% |
|  | Stigmastanol - | 16.3% |
|  | Total | 93.7% |
| Unknown Phytosterols | 2 compounds - | 0.9% |
| Fatty alcohols | C22 - 0.32% | |
|  | C23 - 0.02% | |
|  | C24 - 0.46% | |
|  | C26 - 0.02% | |
|  | Total | ~0.8% |
| Polar impurities | 3–4 compounds - | 4.0% |
| Total |  | ~99.4% |

In preparing the phytosterol compositions of the present invention, the goal in vivo was to increase phytosterol efficacy both intrinsically and extrinsically. As a co-effect of this enhanced efficacy, serum cholesterol levels are decreased.

With respect to the extrinsic effects, it is known that intestinal phytosterol absorption is selective with an inverse relationship existing between phytosterol absorption and cholesterol lowering efficacy (with highly hydrophobic and least absorbable sitostanol being the most effective at lowering cholesterol). Generally, campesterol, which is relatively hydrophilic, is absorbed better than beta-sitosterol with stigmasterol being absorbed minimally. Accordingly, in one aspect of the present invention, a composition is provided in which the beneficial effects (extrinsically and intrinsically) of campesterol are enhanced in an individual to which the composition is administered. In a preferred form, this composition comprises one or more phytosterols which inhibit predominantly cholesterol and beta-sitosterol absorption. In effect, this composition "blocks" or decreases the absorption of beta-sitosterol. In a most preferred form, the present composition comprises one or both of campesterol and sitostanol.

In further embodiment, the compositions of the present invention additionally comprise one or more compounds which inhibit cholesterol synthesis. These compounds include, but are not limited to three-hydroxy-three-methyl glutaryl coenzyme-A (HMG-CoA) reductase inhibitors. The combination of these cholesterol synthesis-limiting compounds and the phytosterol compositions of the present invention is synergistic and initiates and perpetuates both the "intrinsic" and "extrinsic" effects. As cholesterol synthesis and bile cholesterol secretion is decreased, the phytosterol/cholesterol intestinal ratio increases which decreases cholesterol absorption and increases phytosterol transport via the enterocyte shuttle mechanism. The absolute campesterol plasma levels and relative levels of serum campesterol relative to serum beta-sitosterol (the "CSR") are indicative of the functioning of these effects on cholesterol homeostasis. The level of serum campesterol relative to serum Apoprotein-B cholesterol is indicative of the functioning of the phytosterol extrinsic effect on cholesterol homeostasis. The finding of this synergistic co-effect between the phytosterol compositions of the present invention and the compounds which limit cholesterol synthesis, such as statins, is critically important as the dosage of these latter compounds may be significantly reduced when administered in conjunction with the compositions described herein. It has recently been discovered that there are some critical side-effects to statins such as Lovostatins, so the dosage reduction afforded by the synergy with the compositions herein is particularly compelling.

Although the effects of sitostanol on cholesterol enterocyte absorption i.e. the extrinsic effect are most significant as compared to other phytosterols, it is not physiologically beneficial to provide a composition comprising solely sitostanol as the enterocyte shuttle binding with respect to sitostanol is irreversible. In an ideal form, the composition of the present invention maintains the physiological homeostasis of cholesterol and phytosterols without upsetting the enterohepatic shuttle systems.

It is contemplated that the phytosterol compositions of the present invention may he incorporated directly into food or dietary supplements. In a preferred form, the compositions are admixed with a vegetable oil selected from the group comprising safflower oil, sesame seed oil, corn oil, rice bran oil, olive oil and rape seed oil. Supplementing olive oil is most preferred as the oil is widely used and is low in phytosterols and polyunsaturated fatty acids. Alternatively, the compositions may be incorporated into saturated fat (lard)-based products or shortenings such as butter or margarine.

It has also been found that there is a significant co-effect or synergy between the compositions described herein and polyunsaturated fat. Accordingly, oils (such as corn oil) and other foods high in polyunsaturated fats are preferred vehicles or carriers of the compositions to the consumer. In addition, a similar co-effect has been found with respect to saturated fatty acids. Accordingly, foods high in saturated fatty acids are key targets for supplementation with the present composition.

Depending on the mode of delivery of the compositions of the present invention, the dosage may be somewhat varied. It is most preferred that approximately 1.0 g to 3 g be administered daily.

MALE VERSUS FEMALE PROFILE

What is achieved using the protocol variables or markers and the phytosterol compositions describe herein are strategies or models for limiting cholesterol absorption efficiently and without any harmful side-effects.

It has been found, however, that the enterocyte shuttle is gender specific and possesses quantitative (capacity of the plant sterols being absorbed at any given time) and qualitative (composition or selectivity of the plant sterols being absorbed) aspects. In men, the transport capacity of the cholesterol shuttle is increased favouring more hydrophobic plant sterols and cholesterol while in the female, transport capacity is shifted to relatively more hydrophillic (less hydrophobic) dietary sterol components. In patients with metabolism lipid disorders (such as primary familial hyperlipidaemia, etc.) the cholesterol shuttle capacity and relatively higher hydrophobicity exceeds that of the male with increased cholesterol absorption and a reversal of the serum plant sterol ratio from normal plasma campesterol excess to B-sitosterol excess.

Figure 13:
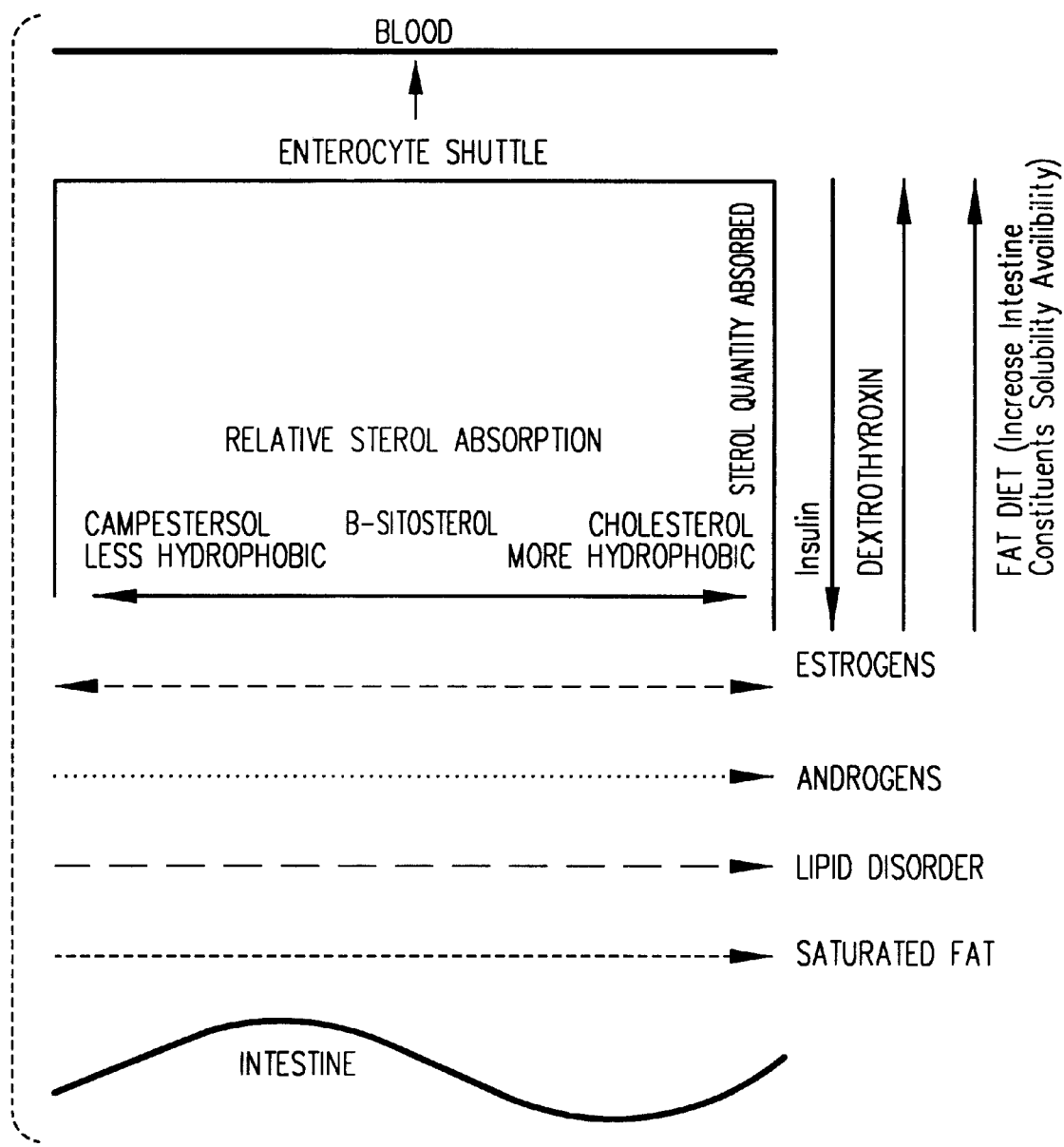
FIG. 13 is a schematic diagram depicting the enterocyte shuttle.

What this means practically is that in males, an increase in cholesterol absorption and in females an increase in plasma triglycerides are the result of a diet high in saturated fat. The qualitative aspect of the cholesterol shuttle capacity refined to herein in relative terms as "less or more hydrophobic" is the result of estrogen and androgen modifying effect on the cholesterol shuttle with estrogen rendering the shuttle less hydrophobic and shifting sterol absorption to the left whereas androgens and metabolic lipid disorders shift to the right towards the less soluble plant sterols as depicted in FIG. 13.

In females, the effects of the administration of the compositions of the present invention initially result in a significant decrease of plasma B-sitosterol and an increase in campesterol with a concomitant high campesterol/B-sitosterol ratio, corresponding to a decrease in intestinal absorption of more hydrophobic sterols. In males, the campesterol/B-sitosterol ratio increase is smaller indicating a shift in male sterol intestinal absorption towards more hydrophobic sterols. Although the campesterol/B-sitosterol ratio is a very significant protocol variable in males and females, it can be said that the key dietary marker of the female pattern is campesterol and the key dietary market of the male pattern is B-sitosterol. Similarly, in patients with lipid disorders, the fractional plant sterol absorption is shifted to the more hydrophobic plant sterol spectrum with B-sitosterol becoming a key plant sterol marker.

In summary, the female pattern is associated with relatively low TC and LDL-C and high HDL-C and high triglycerides. Conversely, the male pattern is associated with high TC and LDL-C and low HDL-C along with low TG. The ratio of campesterol/B-sitosterol is generally higher in the female pattern than in the male pattern. Characteristically, in patients with lipid disorders there is a very low campesterol/B-sitosterol ratio.

As discussed above, there is a clear co-effect between dietary constituents such as polyunsaturated fatty acids and saturated fatty acids and the efficacy of the compositions of the present invention. This co-effect crosses and includes both gender patterns. With respect to the polyunsaturated fatty acid effect in females, there is an improvement in cholesterol profile indicating a co-effect of dietary fatty acids and campesterol with estrogen on the cholesterol enterocyte shuttle. In males, the effect of androgen on cholesterol enterocyte absorption is via a decrease in B-sitosterol and cholesterol and increased campesterol absorption.

GEOGRAPHIC DIETARY PATTERNS

The dietary metabolic studies of the present invention indicate that there are two general dietary patterns:

Type I (Southern or Mediterranean Pattern)

This diet consists of high monounsaturated and saturated fatty acids and low dietary plant sterols, polyunsaturated fatty acids and cholesterol content. The overall cholesterol metabolism of this diet tends to preserve endogenous (internal) cholesterol resources by limiting enterohepatic cholesterol loss. This particular has a high HDL-C. The diet reflecting an increase in tissue demand for cholesterol and a lower TC and LDL-C. The diet cardiovascular risk is low but under adverse metabolic dietary conditions, the diet can be atherogenic.

Type II (Northern or Western Pattern)

This diet consists of high dietary polyunsaturated fatty acids and high plant sterols and cholesterol content. The overall cholesterol metabolism tends to eliminate excess cholesterol by an increase in enterohepatic cholesterol pool losses. The population, generally, has a lower HDL-C, high TC and high LDL-C reflecting a decrease in tissue demand for cholesterol. The diet cardiovascular risk factor is higher than the southern or Mediterranean pattern but under adverse dietary metabolic conditions it can vary.

The consideration of geographic dietary patterns should be included in epidemiological (disease prevention) studies, reproductive and cancer research comparative studies and therapeutic trials. As described herein, the low plasma CSR is best understood as an independent modifiable primary cardiovascular disease risk factor.

EXAMPLES

Example 1

Human Feeding Experiment—General

The aim of this study was to examine how sitostanol-enriched plant sterols added to the diet influence body's level and rate of production of circulating cholesterol. Before study, 10 health normo-lipidemic subjects aged 18–45 were examined by a physician to ensure that they were in good health. Five males and five females were selected. A blood sample (20 mL) were taken for laboratory to confirm the absence of health abnormalities and to measure blood lipid levels. Subjects then consumed a diet provided by the Metabolic Kitchen within the Clinical Research Laboratory for 9 days. This diet contained normal foods and was fed as three meals per day over the 9 day period. To the diet was added at a level of 1.5 g/day of one of: olive oil alone (Olive); olive oil in combination with a composition in accordance with the present invention and comprising sitostanol (Forbes); olive oil in combination with a soybean plant sterol composition (Nulife); or corn oil alone (Corn). These materials were added directly to the diet mixed with a small amount of the dietary oil. This study enabled comparison between data obtained form a separate Heart and Stroke funded research project where the question was to examine whether the higher levels of plan sterols in corn oil were responsible for the cholesterol synthesis-raising action that we previously observed when we fed subjects these oils. In this regard, three diet phases have been studied already; corn (high in phytosterols), olive (very low in phytosterols) and olive with 1.5 g added soybean phytosterols. It is the present objective, in order to use these previous phases as controls, to use olive oil as the dietary oil with added 1.5 g Forbes phytosterols (one of the compositions of the present invention).

Diets were prepared in our metabolic testing facilities, with all meals consumed under supervision by the research staff. Diets were comprised of a two-day rotating menu with food given as three meals per day. The level of food consumed by each subject was formulated to maintain that individual at weight balance, using predictive equations based on the subjects' weight, height, age and sex. Any weight changes were monitored and the amount of food given adjusted accordingly. During the study duration, subjects were given the phone number of a physician that could be contacted should subjects feel any discomfort with the diet.

Over day 9 of the diet period, subjects were requested to drink 25 mL water labelled with a "stable isotope" tag, deuterium oxide. On each of the mornings of days 9 and 10 subjects provided a blood sample (20 mL) for assessment of cholesterol levels and cholesterol synthesis rate. These analyses were conducted by standard procedures. In brief, blood plasma taken at each timepoint over the study was separated and analyzed for total, low density lipoprotein (LDL) and high density lipoprotein (HDL) cholesterol and total triglyceride concentrations. The circulatory levels of plants sterols were also measured as documented. Levels of sitostanol, sitosterol and campesterol were assessed. In addition, cholesterol synthesis was assessed using the rate of uptake of the tracer deuterium from body water into circulating free cholesterol. Analytical methodologies have been described in the literature for these procedures. At the end of the diet period subjects were again examined by a physician to ensure that they were in good health. A portion of the blood sample taken on day 10 was used again to confirm the absence of health abnormalities.

Subjects were tested in two groups of 5. Each group was studied over 10 days. A 4–10 day interval separated the two trials. All procedures were conducted at the Metabolic Testing Facility at the Macdonald Campus of McGill University under the direction of Dr. Peter Jones, Director, Dietetics and Human Nutrition.

Phytosterol Analysis

Plasma phytosterols were extracted and quantitated by gas liquid chromatography (GLC). 5-alpha-cholestane was used as an internal standard. The standard was added to 1.0 ml of plasma and saponified with 50% KOH and methanol (6:94 v/v) for 2 h at 100° C. Plasma was then extracted three times with petroleum ether. Sterols were injected into the GLC (HP 5890 Series II) equipped with flame ionization detection. Separation was achieved on an RTx-1, 30 m capillary column, 0.25 mm ID, 0.25 $\mu$m film thickness (Restek Corp. Bellefont, Pa.). Samples were injected at 80° C. The oven remained for 20 min. The oven temperature then increased to 320° C. (20° C./min) for at least 5 min before subsequent analyses. The injector and detector were set at 1.2 ml/min with the inlet splitter set at 10.:1.

Phytosterol (campesterol, sitosterol, and sitostanol) peak identification was confirmed using authentic standards.

Fractional Synthetic Rate Determination

Deuterium (D) enrichment was measured in red blood cell (RPC) free cholesterol and plasma water. RBC lipid extraction was performed in duplicate. Methanol, hexane/chloroform (4:1 v/v), and doubly distilled water was added to the plasma. The mixtures were shaken mechanically, centrifuged at 1500 rev./min and supernatants were collected. The extraction procedure was repeated and solvent layers were combined. The supernatant was dried under nitrogen and the residue was then dissolved in chloroform and chromatagraphed on silica plates. Plates were developed in hexane/diethyl ether/acetic acid (70:30:1) and the cholesterol band were identified according to a co-chromatagraphed free cholesterol standard. The cholesterol based was scraped from plates and extracted three times by shaking the silica in chloroform for 15 min followed by centrifugation.

Dried cholesterol samples were transferred to 18-cm combustion tubes. Cupric oxide (0.5 g) and a 2-cm length of silver wire were added and tubes were sealed under vacuum of less than 20 mtorr pressure. The cholesterol samples were combusted for 4 hours at 520° C. and the water generated was then vacuum-distilled into 10 cm combustion tubes containing 60 mg zinc reagent. These samples were reduced to zinc oxide and hydrogen gas at 520° C. for 30 min.

Plasma samples were diluted 20 fold with water to reduce D enrichment to within the normal analytical range. Baseline samples were not diluted. Duplicate samples were vacuumdistilled into zinc containing combustion tubes. These plasma water samples were also reduced to zinc oxide and hydrogen gas at 520° C. for 30 min.

The deuterium enrichments of cholesterol and plasma samples were measured by differential isotope ratio mass spectometry using a triple inlet system with electrical H3 compensation. RBC fractional synthetic rate (FSR) values were calculated as cholesterol deuterium enrichment relative to that of the precursor body water pool adjusted for the fraction of hydrogens of cholesterol derived from labelled substrate. The hepatic FSR values were derived using the equation:

$$FSR(\text{per day}) = \frac{\text{chol. enrichment }(100\%_0) * 24\text{h/interval period (h)}}{\text{plasma water enrichment}(100\%_0 * 0.478}$$

The cholesterol enrichment value covers the period of the time between first consumption of deuterated water on the morning of day 9 and when the blood is drawn on the morning of day 10. The multiplication factor of 0.478 accounts for the fraction of deuterium atoms obtained from body water during cholesterogenesis.

FIGURE LEGENDS

FIG. 1 Plasma lipid concentrations of total cholesterol (TOT-C), high density lipoprotein cholesterol (HDL-C), tiglycerides (TG) and low density lipoprotein cholesterol (LDL-C) in healthy male and female subjects (n=11) consuming either Forbes phytosterols and an olive oil based diet (Forbes), Nulife plant sterols and an oliver oil based diet (Nulife), an olive oil diet alone (Olive) or a corn oil diet alone (Corn) for 9 days. Results are expressed as mean ±S.E.M. Diet treatment group means within each parameter having different subscripts differ significantly (p(0.05 using Tukeys post hoc comparison).

FIG. 2 Plasma lipid concentrations of total cholesterol (TOT-C), high density lipoprotein cholesterol (HDL-C), triglycerides (TG) and low density lipoprotein cholesterol (LDL-C) in healthy male subjects (n=6) consuming either Forbes phytosterols and an olive oil based diet (Forbes), Nulife plant sterols and an olive oil based diet (Nulife), an olive oil diet along (Olive) or a corn diet alone (Corn) for 9 days. Results are expressed as mean ±S.E.M. Diet treatment group means within each parameter having different subscripts differ significantly (p(0.05 using Tukeys post hoc comparison).

FIG. 3 Plasma lipid concentrations of total cholesterol (TOT-C), high density lipoprotein cholesterol (HDL-C), triglycerides (TG) and low density lipoprotein cholesterol (LDL-C) in healthy female subjects (n=5) consuming either Forbes phytosterols and an olive oil based diet (Forbes), Nulife plant sterols and an olive oil based diet (Nulife), an olive oil diet along (Olive) or a corn diet alone (Corn) for 9 days. Results are expressed as mean ±S.E.M.

Diet treatment group means within each parameter having different subscripts differ significantly (p(0.05 using Tukeys post hoc comparison).

FIG. 4 Decrease in plasma lipid concentrations of total cholesterol (TOT-C), high density lipoprotein cholesterol (HDL-C), triglycerides (TG) and low density lipoprotein cholesterol (LDL-C) in healthy male and female subjects (n=11) consuming either Forbes phytosterols and an olive oil based diet (Forbes), Nulife plant sterols and an olive oil based diet (Nulife), an olive oil diet alone (Olive) or a corn oil diet alone (Corn) for 9 days compared to plasma lipid concentrations prior to diet treatment. Results are expressed as mean ±S.E.M. Diet treatment group means within each parameter having different subscripts differ significantly (p(0.05 using Tukeys post hoc comparison).

FIG. 5 Decrease in plasma lipid concentrations of total cholesterol (TOT-C), high density lipoprotein cholesterol (RDL-C), triglycerides (TG) and low density lipoprotein cholesterol (LDL-C) in healthy male subjects (n=6) consuming either Forbes phytosterols and an olive oil based diet (Forbes), Nulife plant sterols and an olive oil based diet (Nulife), an olive oil diet alone (Olive) or a corn oil diet alone (Corn) for 9 days compared to plasma lipid concentrations prior to diet treatment. Results are expressed as mean ±S.E.M. Diet treatment group means within each parameter having different subscripts differ significantly (p(0.05 using Tukeys post hoc comparison).

FIG. 6 Decrease in plasma lipid concentrations of total cholesterol (TOT-C), high density lipoprotein cholesterol (HDL-C), triglycerides (TG) and low density lipoprotein cholesterol (LDL-C) in healthy female subjects (n=5) consuming either Forbes phytosterols and an olive oil based diet (Forbes), Nulife plant sterols and an oliver based diet (Nulife), an olive oil diet along (Olive) or a corn oil diet alone (Corn) for 9 days compared to plasma lipid concentrations prior to diet treatment. Results are expressed as mean ±S.E.M. Diet treatment group means within each parameter having different subscripts differ significantly (p(0.05 using Tukeys post hoc comparison).

FIG. 7 shows the concentration of individual phytosterols in plasma of subjects consuming either a Forbes (present invention) and olive oil based diet, Nulife phytosterols and olive oil base diet, olive oil diet alone (Olive) and corn oil diet along (corn).

RESULTS

The results of these human clinical trials ware outlined in the following Tables 1–20 and further compiled into FIGS. 1–7.

Mean plasma total cholesterol concentration in the Forbes phytosterol supplemented group was significantly lower than that for the olive oil group. It was also lower, though non-significantly, than the Nulife Phytosterol supplemented group (Table 1, FIG. 1).

Mean HDL cholesterol concentration was highest in the Forbes phytosterol group. However, this difference was non-significant relative to the other groups due to much variation among subjects within groups (Table 2, FIG. 1).

Mean triglyceride levels were lower in the group fed corn oil than that consuming the Nulife sterols (Table 3, FIG. 1).

Mean LDL cholesterol concentration in the Forbes phytosterol supplemented group was significantly lower than the mean concentrations for both the Nulife and oil groups (Table 4, FIG. 1).

Within the male subset of subjects, total cholesterol levels were significantly different between the Forbes and olive oil groups and between corn oil and Nulife groups. LDL cholesterol levels were significantly different between the Forbes and Nulife groups, the Forbes and olive oil groups, and olive oil and corn oil/groups. There was no statistical significance between treatment groups for the female subjects (FIGS. 2, 3).

FSR values were highest in the Forbes phytosterol group. This difference is significant with respect to the olive oil group. Nulife means FSR is substantially lower than the Forbes mean FSR. However, the difference is non-significant due to much variation within the Nulife group (FIG. 4).

The mean values in the corn oil group for each of the preceding parameters were in all cases minimally or non-significantly different from the Forbes mean values.

Results of the GLC analysis indicate absorption of phytosterols (campesterol and sitosterol) from the intestine into the bloodstream is lowest in the Forbes phytosterol supplemented group. The corn group demonstrated high concentrations of phytosterols in plasma, and thus the greatest absorption of phytosterols into the blood stream. Olive and Nulife groups demonstrated similar intermediate plasma phytosterol concentrations (FIG. 5). Plasma campesterol concentrations following the Forbes treatment diet were significantly different from those following the Nulife and corn treatment diets. Sitosterol concentrations in the Forbes group were significantly different from those in all other treatment groups.

Correlational analyses were performed to examine for relationships between circulating phytosterol levels and indices of lipid level and synthesis (Table 9–13). Significant associations were observed between campesterol and HDL cholesterol concentration in the FCP group, between sitosterol and LDL cholesterol and between campesterol and total and LDL cholesterol level in the olive oil group. In corn oil fed individuals, sitostanol was correlated to HDL cholesterol levels also.

Individual data points for all subjects and males versus females for circulating campesterol, sitosterol, campesterol/ sitosterol ratio, total cholesterol, HDL cholesterol and LDL cholesterol, as well as PSR are provided for subjects on each dietary trial in Tables 9–20.

TABLE 1

Plasma Cholesterol Concentration (mg/dl) following Diet Treatment

| | | Diet Treatment | | | |
|---|---|---|---|---|---|
| Subject | Sex | Forbes | Nulife | Olive | Corn |
| 1 | M | 143.6 | 154.2 | 153.6 | 126.3 |
| 2 | M | 112.6 | 115.1 | 126.2 | 110.4 |
| 3 | M | 116.4 | 119.4 | 116.7 | 107.3 |
| 4 | M | 136.5 | 138.8 | 142.0 | 136.0 |
| 5 | M | 104.9 | 124.7 | 116.8 | 115.7 |
| 6 | M | 108.4 | 110.0 | 122.7 | 103.1 |
| subtotal | mean ± | 120.4$^{ac}$ ± | 127.0$^{ab}$ ± | 129.7$_b$ ± | 116.5$^c$ ± |
| | SEM | 6.5 | 6.8 | 6.1 | 5.1 |
| 7 | F | 144.9 | 163.9 | 114.8 | 119.8 |
| 8 | F | 94.6 | 117.9 | 177.2 | 106.9 |
| 9 | F | 146.1 | 154.4 | 137.4 | 135.3 |
| 10 | F | 146.0 | 146.9 | 133.4 | 136.3 |
| 11 | F | 120.4 | 126.9 | 140.7 ± 13.1 | 116.1 |
| subtotal | mean ± | 130.4 ± | 142.0 ± | 134.1$^b$ ± | 122.9 ± |
| | SEM | 10.2 | 8.6 | 6.2 | 5.7 |
| TOTAL | mean ± | 124.9$^a$ ± | 133.8$^b$ ± | | 119.4$^2$ ± |
| | SEM | 5.7 | 5.6 | | 3.7 |

Plasma total cholesterol concentration in healthy male and female subjects (n = 11) consuming either Forbes phytosterols and an olive oil based diet (Forbes), Nulife phytosterols and an olive oil based diet (Nulife), an olive oil diet alone (Olive) or a corn oil diet alone (Corn) for 9 days. Diet treatment group means within each parameter having different subscripts differ significantly ($p < 0.05$ using Tukeys post hoc comparison).

TABLE 2

Plasma High Density Lipoprotein Cholesterol Concentration (mg/dl) following Diet Treatment

| | | Diet Treatment | | | |
|---|---|---|---|---|---|
| Subject | Sex | Forbes | Nulife | Olive | Corn |
| 1 | M | 49.1 | 41.4 | 32.7 | 28.6 |
| 2 | M | 35.0 | 37.5 | 33.7 | 32.5 |
| 3 | M | 40.5 | 29.1 | 34.8 | 33.6 |
| 4 | M | 33.0 | 36.5 | 40.7 | 35.0 |
| 5 | M | 40.0 | 41.1 | 39.2 | 42.1 |
| 6 | M | 50.5 | 46.0 | 47.0 | 46.0 |
| subtotal | mean ± | 41.3 ± | 38.6 ± | 38.0 ± | 36.3 ± |
| | SEM | 2.9 | 2.3 | 2.2 | 2.6 |
| 7 | F | 49.3 | 50.1 | | 36.7 |
| 8 | F | 36.3 | 44.1 | 44.5 | 44.8 |
| 9 | F | 39.1 | 39.1 | 42.7 | 34.4 |
| 10 | F | 65.2 | 58.5 | 50.9 | 57.6 |
| 11 | F | 49.1 | 48.3 | 47.0 | 49.7 |
| subtotal | mean ± | 47.8 ± | 48.0 ± | 46.3 ± | 44.6 ± |
| | SEM | 5.1 | 3.2 | 1.8 | 4.3 |
| TOTAL | mean ± | 44.2$^a$ ± | 42.8 ± | 41.3 ± | 40.1$^b$ ± |
| | SEM | 2.8 | 2.4 | 2.6 | 2.6 |

Plasma high density lipoprotein cholesterol concentration in healthy male and female subjects (n = 11) consuming either Forbes phytosterols and an olive oil based diet (Forbes), Nulife phytosterols and an olive oil based diet (Nulife), an olive oil diet alone (Olive) or a corn oil diet alone (Corn) for 9 days. Diet treatment group means within each parameter having different subscripts differ significantly ($p < 0.05$ using Tukeys post hoc comparison).

TABLE 3

Plasma Triglyceride Concentration (mg/dl) following Diet Treatment

| | | Diet Treatment | | | |
|---|---|---|---|---|---|
| Subject | Sex | Forbes | Nulife | Olive | Corn |
| 1 | M | 48.0 | 59.7 | 69.2 | 60.4 |
| 2 | M | 55.3 | 56.4 | 43.7 | 46.2 |
| 3 | M | 67.5 | 95.4 | 58.7 | 81.8 |
| 4 | M | 91.5 | 70.5 | 60.1 | 76.4 |
| 5 | M | 77.5 | 59.6 | 62.6 | 41.7 |
| 6 | M | 74.7 | 82.7 | 97.4 | 86.0 |
| subtotal | mean ± | 69.1 ± | 70.7 ± | 65.3 ± | 65.4 ± |
| | SEM | 6.4 | 6.3 | 7.3 | 7.7 |
| 7 | F | 62.5 | 59.8 | | 44.7 |
| 8 | F | 99.6 | 130.1 | 85.5 | 83.1 |
| 9 | F | 57.8 | 105.3 | 135.9 | 84.9 |
| 10 | F | 65.3 | 60.9 | 62.7 | 50.6 |
| 11 | F | 55.2 | 78.0 | 83.8 | 52.8 |
| subtotal | mean ± | 68.1 ± | 86.8 ± | 92.0 ± | 63.2 ± |
| | SEM | 8.1 | 13.6 | 15.5 | 8.6 |
| TOTAL | mean ± | 68.6 ± | 78.0$^2$ ± | 76.0 ± | 64.4$^b$ ± |
| | SEM | 4.8 | 7.1 | 8.3 | 5.4 |

Plasma triglyceride concentration in healthy male and female subjects (n = 11) consuming either Forbes phytosterols and an olive oil based diet (Forbes), Nulife phytosterols and an olive oil based diet (Nulife), an olive oil diet alone (Olive) or a corn oil diet alone (Corn) for 9 days. Diet treatment group means within each parameter having different subscripts differ significantly ($p < 0.05$ using Tukeys post hoc comparison).

TABLE 4

Plasma Low Density Lipoprotein Cholesterol Concentration (mg/dl) following Diet Treatment

| | | Diet Treatment | | | |
|---|---|---|---|---|---|
| Subject | Sex | Forbes | Nulife | Olive | Corn |
| 1 | M | 84.8 | 100.8 | 107.1 | 85.5 |
| 2 | M | 66.5 | 66.3 | 83.7 | 68.7 |
| 3 | M | 62.4 | 71.2 | 70.2 | 57.4 |
| 4 | M | 85.2 | 88.2 | 89.3 | 85.8 |
| 5 | M | 49.8 | 71.8 | 65.1 | 65.3 |
| 6 | M | 42.9 | 47.4 | 56.3 | 39.8 |
| subtotal | mean ± | 65.3$^3$ ± | 74.3$^{bc}$ ± | 78.6$^6$ ± | 67.1$^{bc}$ ± |
| | SEM | 7.1 | 7.5 | 7.5 | 7.2 |
| 7 | F | 83.1 | 101.9 | | 74.1 |
| 8 | F | 38.4 | 47.8 | 53.2 | 45.5 |
| 9 | F | 95.4 | 94.3 | 107.3 | 84.0 |
| 10 | F | 66.3 | 75.8 | 74.0 | 97.4 |
| 11 | F | 60.3 | 63.0 | 69.6 | |
| subtotal | mean ± | 68.7 ± | 76.5 ± | 76.0 ± | 71.3 ± |
| | SEM | 9.8 | 9.9 | 11.3 | 9.4 |
| TOTAL | mean ± | 68.8$^a$ ± | 75.3$^b$ ± | 77.6$^b$ ± | 69.0$^{ac}$ ± |
| | SEM | 5.6 | 5.8 | 6.0 | 5.5 |

Plasma low density lipoprotein cholesterol concentration in healthy male and female subjects (n = 11) consuming either Forbes phytosterols and an olive oil based diet (Forbes), Nulife phytosterols and an olive oil based diet (Nulife), an olive oil diet alone (Olive) or a corn oil diet alone (Corn) for 9 days. Diet treatment group means within each parameter having different subscripts differ significantly ($p < 0.05$ using Tukeys post hoc comparison).

TABLE 5

Decrease in Plasma Cholesterol Concentration (mg/dl) following Diet Treatment Compared to Baseline

| | | Diet Treatment | | | |
|---|---|---|---|---|---|
| Subject | Sex | Forbes | Nulife | Olive | Corn |
| 1 | M | 18.4 | 7.8 | 8.4 | 35.7 |
| 2 | M | 27.7 | 25.2 | 14.1 | 29.9 |

TABLE 5-continued

Decrease in Plasma Cholesterol Concentration (mg/dl) following Diet Treatment Compared to Baseline

| Subject | Sex | Forbes | Nulife | Olive | Corn |
|---|---|---|---|---|---|
| 3 | M | 18.0 | 15.0 | 17.6 | 27.0 |
| 4 | M | 22.5 | 20.3 | 17.1 | 23.1 |
| 5 | M | 9.6 | −10.2 | −2.3 | −1.2 |
| 6 | M | 19.6 | 17.9 | 5.2 | 24.9 |
| subtotal | mean ± | 19.3$^{ac}$ ± | 12.7$^{ab}$ ± | 10.0$^b$ ± | 23.2 ± |
|  | SEM | 2.4 | 5.2 | 3.2 | 5.2 |
| 7 | F | 0.1 | −18.9 |  | 25.3 |
| 8 | F | 53.9 | 30.6 | 33.8 | 41.7 |
| 9 | F | 32.0 | 23.7 | 1.0 | 42.8 |
| 10 | F | 4.6 | 3.7 | 13.2 | 14.4 |
| 11 | F | 49.8 | 43.3 | 36.7 | 54.0 |
| subtotal | mean ± | 28.1 ± | 16.5$^{ab}$ ± | 21.2 ± | 35.6 ± |
|  | SEM | 11.1 | 10.9 | 8.5 | 7.0 |
| TOTAL | mean ± | 23.3$^a$ ± | 14.4$_b$ ± | 14.4$_b$ ± | 28.8$^a$ ± |
|  | SEM | 5.1 | 5.4 | 4.0 | 4.5 |

Decrease in plasma cholesterol concentration in healthy male and female subjects (n = 11) consuming either Forbes phytosterols and an olive oil based diet (Forbes), Nulife phytosterols and an olive oil based diet (Nulife), an olive oil diet alone (Olive) or a corn oil diet alone (Corn) for 9 days compared to plasma lipid concentrations prior to diet treatment. Diet treatment group means within each parameter having different subscripts differ significantly (p < 0.05 using Tukeys post hoc comparison).

TABLE 6

Decrease in Plasma High Density Lipoprotein Cholesterol Concentration (mg/dl) following Diet Treatment Compared to Baseline

| Subject | Sex | Forbes | Nulife | Olive | Corn |
|---|---|---|---|---|---|
| 1 | M | −13.5 | −5.8 | 2.94 | 7.0 |
| 2 | M | 16.9 | 14.4 | 18.1 | 19.4 |
| 3 | M | 26.5 | 37.9 | 32.2 | 33.4 |
| 4 | M | 15.5 | 12.0 | 7.9 | 13.5 |
| 5 | M | 13.1 | 11.7 | 13.5 | 10.6 |
| 6 | M | 0.4 | 4.9 | 4.0 | 4.9 |
| subtotal | mean ± | 9.8 ± | 12.5 ± | 13.1 ± | 14.8 ± |
|  | SEM | 5.8 | 5.9 | 4.5 | 4.3 |
| 7 | F | 16.6 | 15.8 |  | 29.3 |
| 8 | F | 45.8 | 38.0 | 37.6 | 37.3 |
| 9 | F | 13.5 | 13.5 | 9.9 | 18.2 |
| 10 | F | 5.11 | 1.6 | 9.2 | 2.5 |
| 11 | F | 6.6 | 7.3 | 8.6 | 5.9 |
| subtotal | mean ± | 15.5 ± | 15.3 ± | 16.3 ± | 18.6 ± |
|  | SEM | 8.4 | 6.2 | 7.1 | 6.7 |
| TOTAL | mean ± | 12.4$^a$ ± | 13.8 ± | 14.4 ± | 16.5$^b$ ± |
|  | SEM | 4.8 | 4.1 | 3.7 | 3.7 |

Decrease in plasma high density lipoprotein cholesterol concentration in healthy male and female subjects (n = 11) consuming either Forbes phytosterols and an olive oil based diet (Forbes), Nulife phytosterols and an olive oil based diet (Nulife), an olive oil diet alone (Olive) or a corn oil diet alone (Corn) for 9 days compared to plasma lipid concentrations prior to diet treatment. Diet treatment group means within each parameter having different subscripts differ signficantly (p < 0.05 using Tukeys post hoc comparison).

TABLE 7

Decease in Plasma Triglyceride Concentration (mg/dl) following Diet Treatment

| Subject | Sex | Forbes | Nulife | Olive | Corn |
|---|---|---|---|---|---|
| 1 | M | −9.9 | −21.5 | −31.0 | −22.3 |
| 2 | M | −26.5 | −27.6 | −14.9 | −17.4 |
| 3 | M | 5.5 | −22.4 | 14.3 | −8.8 |
| 4 | M | −26.6 | −5.5 | 4.8 | −11.4 |
| 5 | M | −30.3 | −2.4 | −15.5 | 5.5 |
| 6 | M | −13.0 | −21.1 | −35.7 | −24.4 |
| subtotal | mean ± | −16.8 ± | −18.4 ± | −13.0 ± | −13.1 ± |
|  | SEM | 5.6 | 3.3 | 8.0 | 4.5 |
| 7 | F | 0.7 | 3.4 |  | 18.5 |
| 8 | F | −6.3 | −36.8 | 7.8 | 10.2 |
| 9 | F | 42.8 | −4.6 | −35.3 | 15.7 |
| 10 | F | 3.0 | 7.4 | 5.5 | 17.7 |
| 11 | F | 25.7 | 2.9 | −2.9 | 28.1 |
| subtotal | mean ± | 13.2 ± | −5.6 ± | −6.2 ± | 18.0 ± |
|  | SEM | 9.1 | 8.0 | 10.0 | 2.9 |
| TOTAL | mean ± | −3.173 ± | −12.6$^a$ ± | −10.3 ± | 1.0$^b$ ± |
|  | SEM | 6.8 | 4.3 | 6.0 | 5.6 |

Decrease in plasma triglyceride concentration in healthy male and female subjects (n = 11) consuming either Forbes phytosterols and an olive oil based diet (Forbes), Nulife phytosterols and an olive oil based diet (Nulife), an olive oil diet alone (Olive) or a corn oil diet alone (Corn) for 9 days compared to plasma lipid concentrations prior to diet treatment. Diet treatment group means within each parameter having different subscripts differ significantly (p < 0.05 using Tukeys post hoc comparison).

TABLE 8

Decrease in Plasma Low Density Lipoprotein Cholesterol Concentration (mg/dl) following Diet Treatment Compared to Baseline

| Subject | Sex | Forbes | Nulife | Olive | Corn |
|---|---|---|---|---|---|
| 1 | M | 33.9 | 17.9 | 11.6 | 33.2 |
| 2 | M | 16.1 | 16.3 | −1.1 | 13.9 |
| 3 | M | −9.7 | −18.5 | −17.5 | −4.6 |
| 4 | M | 12.4 | 9.3 | 8.3 | 11.8 |
| 5 | M | 2.5 | −19.4 | −12.7 | −12.9 |
| 6 | M | 21.7 | 17.2 | 8.4 | 24.8 |
| subtotal | mean ± | 12.8$^a$ ± | 3.8$^{bc}$ ± | −0.5$^b$ ± | 11.0$^{ac}$ ± |
|  | SEM | 6.2 | 7.3 | 5.0 | 7.1 |
| 7 | F | −16.6 | −35.4 |  | −7.7 |
| 8 | F | 9.4 | 0.0 | −5.4 | 2.3 |
| 9 | F | 10.0 | 11.1 | −1.9 | 21.5 |
| 10 | F | 10.6 | 1.1 | 2.9 | −20.5 |
| 11 | F | 38.0 | 35.3 | 28.7 | 42.5 |
| subtotal | mean ± | 10.3 ± | 2.4 ± | 6.1 ± | 7.6 ± |
|  | SEM | 8.6 | 11.4 | 7.2 | 11.1 |
| TOTAL | mean ± | 11.7$^a$ ± | 3.2$^{bc}$ ± | 2.1$^b$ ± | 9.5$^{ac}$ ± |
|  | SEM | 4.9 | 6.2 | 4.2 | 6.0 |

Decrease in plasma low density lipoprotein cholesterol concentration in healthy male and female subjects (n = 11) consuming either Forbes phytosterols and an olive oil based diet (Forbes), Nulife phytosterols and an olive oil based diet (Nulife), an olive oil diet alone (Olive) or a corn oil diet alone (Corn) for 9 days compared to plasma lipid concentrations prior to diet treatment. Diet treatment group means within each parameter having different subscripts differ significantly (p < 0.05 using Tukeys post hoc comparison).

TABLE 9

FORBES PHYTOSTEROLS

| SAMPLES Name | Campest mg/dl | sitoste mg/dl | FSR pools/d | LDL mg/dl | HDL mg/dl | Tot. chol mg/dl | camp/sit |
|---|---|---|---|---|---|---|---|
| Alan | 0.30 | 0.13 | 5.30 | 66.5 | 35.00 | 112.60 | 2.34 |
| Dave | 1.11 | 0.68 | 6.3 | 42.9 | 50.50 | 108.40 | 1.54 |
| Elizabeth | 1.16 | 0.59 | 4.00 | 60.3 | 49.10 | 120.40 | 1.94 |
| Grant | 3.46 | 1.63 | 2.60 | 84.8 | 49.10 | 143.60 | 2.12 |
| Joban | 1.35 | 1.33 | 5.30 | 85.2 | 33.00 | 136.50 | 1.02 |
| John | 0.28 | 0.23 | 5.20 | 49.8 | 40.00 | 104.90 | 1.22 |
| Manon | 0.37 | 0.13 | 4.70 | 83.1 | 49.30 | 144.90 | 2.92 |
| Mary | | | 5.90 | 66.3 | 65.20 | 146.00 | |
| Paula | | | 3.20 | 95.4 | 39.10 | 146.10 | |
| Patrice | | | 5.00 | 62.4 | 40.50 | 116.40 | |
| Stephanie | 0.52 | 0.12 | 7.60 | 38.4 | 36.30 | 94.60 | 4.46 |
| MEAN | 1.07 | 0.60 | 5.01 | 66.83 | 44.28 | 124.95 | 2.21 |
| STD | 0.99 | 0.55 | 1.33 | 17.77 | 8.97 | 18.12 | 1.03 |

TABLE 10

OLIVE

| SAMPLES Name | Campest mg/dl | sitoste mg/dl | FSR pools/d | LDL mg/dl | HDL mg/dl | Tot. chol mg/dl | camp/sit |
|---|---|---|---|---|---|---|---|
| Dave | 6.20 | 7.80 | | 56.3 | 47.00 | 122.70 | 0.79 |
| Elizabeth | 8.30 | 9.40 | | 69.6 | 47.00 | 133.40 | 0.88 |
| Joban | 3.60 | 7.60 | | 89.3 | 40.70 | 142.00 | 0.47 |
| John | 6.90 | 15.60 | | 65.1 | 39.20 | 116.80 | 0.44 |
| Mary | 4.30 | 9.80 | | 74 | 50.90 | 137.40 | 0.44 |
| Paula | | | | 107.3 | 42.70 | 114.80 | |
| Patrice | 4.80 | 5.40 | | 70.2 | 34.80 | 116.70 | 0.89 |
| Stephanie | 14.40 | 14.10 | | 53.2 | 44.50 | 114.80 | 1.02 |
| Grant | 3.13 | 3.23 | 1.30 | 107.10 | 32.70 | 153.60 | 0.97 |
| MEAN | 6.45 | 9.12 | 1.30 | 76.90 | 42.17 | 128.02 | 0.74 |
| STD | 3.42 | 3.87 | 0.00 | 18.92 | 5.61 | 13.33 | 0.23 |

TABLE 11

PLANT STEROL

| SAMPLES Name | Campest mg/dl | sitoste mg/dl | FSR pools/d | LDL mg/dl | HDL mg/dl | Tot. chol mg/dl | camp/sit |
|---|---|---|---|---|---|---|---|
| Dave | 6.60 | 7.50 | | 47.4 | 46.00 | 110.00 | 0.88 |
| Elizabeth | 5.70 | 5.90 | | 63 | 48.30 | 126.90 | 0.97 |
| Johan | 4.70 | 10.20 | | 88.2 | 36.50 | 138.80 | 0.46 |
| John | 10.30 | 12.60 | | 71.8 | 41.10 | 124.70 | 0.82 |
| Mary | 11.00 | 13.20 | | 75.8 | 58.50 | 146.90 | 0.83 |
| Paula | 12.00 | 14.50 | | 94.3 | 39.10 | 135.30 | 0.83 |
| Patrice | 4.20 | 4.80 | | 71.2 | 29.10 | 119.40 | 0.88 |
| Stephanie | 12.90 | 14.40 | | 47.8 | 44.10 | 117.90 | 0.90 |
| Alan | | | 1.60 | 66.30 | 37.50 | 115.10 | |
| Grant | 2.48 | 4.54 | 0.60 | 100.80 | 41.40 | 154.20 | 0.55 |
| MEAN | 7.76 | 9.74 | 1.10 | 72.66 | 42.16 | 128.92 | 0.79 |
| STD | 3.60 | 3.89 | 0.50 | 17.04 | 7.47 | 13.72 | 0.16 |

TABLE 12

CORN

| SAMPLES Name | Campest mg/dl | sitoste mg/dl | FSR pools/d | LDL mg/dl | HDL mg/dl | Tot. chol mg/dl | camp/sit |
|---|---|---|---|---|---|---|---|
| Dave | 9.70 | 10.50 | | 39.8 | 46.00 | 103.10 | 0.92 |
| Elizabeth | 9.30 | 11.50 | | 55.8 | 49.70 | 116.10 | 0.81 |
| Johan | 13.90 | 7.00 | | 85.8 | 35.00 | 136.00 | 1.99 |
| John | 12.30 | 13.90 | | 65.3 | 42.10 | 116.70 | 0.88 |
| Mary | 18.40 | 21.50 | | 97.4 | 57.60 | 136.30 | 0.86 |
| Paula | 6.70 | 7.00 | | 84 | 34.40 | 135.30 | 0.96 |
| Patrice | 5.50 | 5.60 | | 57.4 | 33.60 | 107.30 | 0.98 |
| Stephanie | 4.40 | 10.00 | | 45.5 | 44.80 | 106.90 | 0.44 |
| Alan | | | 7.10 | 68.70 | 32.50 | 110.40 | |
| Grant | 10.96 | 9.91 | 2.10 | 85.50 | 28.60 | 126.30 | 1.11 |
| MEAN | 10.13 | 10.77 | 4.60 | 68.52 | 40.43 | 119.34 | 1.00 |
| STD | 4.15 | 4.50 | 2.50 | 18.20 | 8.65 | 12.39 | 0.41 |

TABLE 13

FORBES PHYTOSTE: MALES

| SAMPLES Name | Campest mg/dl | sitoste mg/dl | FSR pools/d | LDL mg/dl | HDL mg/dl | Tot. chol mg/dl | camp/sit |
|---|---|---|---|---|---|---|---|
| Alan | 0.30 | 0.13 | 5.30 | 66.5 | 35.00 | 112.60 | 2.34 |
| Dave | 1.11 | 0.68 | 6.3 | 42.9 | 50.50 | 108.40 | 1.64 |
| Grant | 3.46 | 1.63 | 2.60 | 84.8 | 49.10 | 143.60 | 2.12 |
| Johan | 1.35 | 1.33 | 5.30 | 85.2 | 33.00 | 136.50 | 1.02 |
| John | 0.28 | 0.23 | 5.20 | 49.8 | 40.00 | 104.90 | 1.22 |
| Patrice | | | 5.00 | 62.4 | 40.50 | 116.40 | |
| MEAN | 1.30 | 0.80 | 4.95 | 65.27 | 41.35 | 120.40 | 1.67 |
| STD | 3.60 | 0.59 | 1.13 | 15.96 | 6.54 | 14.48 | 0.51 |

TABLE 14

FORBES PHYTOSTE: FEMALES

| SAMPLES Name | Campest mg/dl | sitoste mg/dl | FSR pools/d | LDL mg/dl | HDL mg/dl | Tot. chol mg/dl | camp/sit |
|---|---|---|---|---|---|---|---|
| Elizabeth | 1.16 | 0.59 | 4.00 | 60.3 | 49.10 | 120.40 | 1.94 |
| Manon | 0.37 | 0.13 | 4.70 | 83.1 | 49.30 | 144.90 | 2.92 |
| Mary | | | 5.90 | 66.3 | 65.20 | 146.00 | |
| Paula | | | 3.20 | 95.4 | 39.10 | 146.10 | |
| Stephanie | 0.52 | 0.12 | 7.60 | 38.4 | 36.30 | 94.60 | 4.46 |
| MEAN | 0.68 | 0.28 | 5.08 | 68.70 | 47.80 | 130.40 | 3.11 |
| STD | 0.34 | 0.22 | 1.54 | 19.57 | 10.15 | 20.40 | 1.04 |

TABLE 15

OLIVE: MALES

| SAMPLES Name | Campest mg/dl | sitoste mg/dl | FSR pools/d | LDL mg/dl | HDL mg/dl | Tot. chol mg/dl | camp/sit |
|---|---|---|---|---|---|---|---|
| Dave | 6.20 | 7.80 | | 56.3 | 47.00 | 122.70 | 0.79 |
| Johan | 3.60 | 7.60 | | 89.3 | 40.70 | 142.00 | 0.47 |
| John | 6.90 | 15.60 | | 55.1 | 39.20 | 116.80 | 0.44 |
| Patrice | 4.80 | 5.40 | | 70.2 | 34.80 | 116.70 | 0.89 |
| Alex | 3.43 | 1.21 | 2.60 | 91.90 | 42.30 | 148.15 | 2.82 |
| Grant | 3.13 | 3.23 | 1.30 | 107.10 | 32.70 | 153.60 | 0.97 |
| Jean | 3.02 | 1.19 | 1.30 | 96.80 | 40.80 | 148.50 | 2.53 |
| MEAN | 4.44 | 6.00 | 1.73 | 82.39 | 39.64 | 135.49 | 1.27 |
| STD | 1.45 | 4.66 | 0.61 | 17.26 | 4.40 | 14.96 | 0.91 |

TABLE 16

OLIVE: FEMALES

| SAMPLES Name | Campest mg/dl | sitoste mg/dl | FSR pools/d | LDL mg/dl | HDL mg/dl | Tot. chol mg/dl | camp/sit |
|---|---|---|---|---|---|---|---|
| Elizabeth | 8.30 | 9.40 | | 69.5 | 47.00 | 133.40 | 0.88 |
| Mary | | | | | | | |
| Paula | | | | 107.3 | 42.70 | 114.80 | |
| Stephanie | 14.40 | 14.10 | | 53.2 | 44.50 | 114.80 | 1.02 |
| Lucy | 0.81 | 0.60 | 3.70 | 89.40 | 68.70 | 174.00 | 1.35 |
| MEAN | 7.84 | 8.03 | 3.70 | 79.88 | 50.73 | 134.25 | 1.08 |
| STD | 5.56 | 5.60 | 0.00 | 20.37 | 10.49 | 24.17 | 0.20 |

TABLE 17

PLANT: MALES

| SAMPLES (Nulife) Name | Campest mg/dl | sitoste mg/dl | FSR pools/d | LDL mg/dl | HDL mg/dl | Tot. chol mg/dl | camp/sit |
|---|---|---|---|---|---|---|---|
| Dave | 6.60 | 7.50 | | 47.4 | 46.00 | 110.00 | 0.88 |
| Johan | 4.70 | 10.20 | | 88.2 | 36.50 | 138.80 | 0.46 |
| John | 10.30 | 12.60 | | 71.8 | 41.10 | 124.70 | 0.82 |
| Patrice | 4.20 | 4.80 | | 71.2 | 29.10 | 119.40 | 0.88 |
| Alan | | | 1.60 | 66.30 | 37.50 | 115.10 | |
| Grant | 2.48 | 4.54 | 0.60 | 100.80 | 41.40 | 154.20 | 0.55 |
| Jean | | | 0.50 | 87.90 | 41.90 | 139.20 | |
| MEAN | 5.66 | 7.93 | 0.90 | 76.23 | 39.07 | 128.77 | 0.72 |
| STD | 2.67 | 3.11 | 0.50 | 16.29 | 4.99 | 14.84 | 0.18 |

TABLE 18

PLANT: FEMALES

| SAMPLES (Nulife) Name | Campest mg/dl | sitoste mg/dl | FSR pools/d | LDL mg/dl | HDL mg/dl | Tot. chol mg/dl | camp/sit |
|---|---|---|---|---|---|---|---|
| Elizabeth | 5.70 | 5.90 | | 63 | 48.30 | 126.90 | 0.97 |
| Mary | 11.00 | 13.20 | | 75.8 | 68.50 | 146.90 | 0.83 |
| Paula | 12.00 | 14.50 | | 94.3 | 39.10 | 135.30 | 0.83 |
| Stephanie | 12.90 | 14.40 | | 47.6 | 44.10 | 117.90 | 0.90 |
| Lucy | | | 5.60 | 91.80 | 42.80 | 147.20 | |
| MEAN | 10.40 | 12.00 | 5.60 | 74.54 | 46.56 | 134.84 | 0.88 |
| STD | 2.80 | 3.56 | 0.00 | 17.54 | 6.65 | 11.39 | 0.08 |

TABLE 19

CORN: MALES

| SAMPLES Name | Campest mg/dl | sitoste mg/dl | FSR pools/d | LDL mg/dl | HDL mg/dl | Tot. chol mg/dl | camp/sit |
|---|---|---|---|---|---|---|---|
| Dave | 9.70 | 10.50 | | 39.8 | 46.00 | 103.10 | 0.92 |
| Johan | 13.90 | 7.00 | | 85.8 | 35.00 | 136.00 | 1.99 |
| John | 12.30 | 13.90 | | 65.3 | 42.10 | 115.70 | 0.88 |
| Patrice | 5.50 | 5.60 | | 57.4 | 33.60 | 107.30 | 0.98 |
| Alan | 6.32 | 2.33 | 7.10 | 68.70 | 32.50 | 110.40 | 2.71 |
| Grant | 10.96 | 9.91 | 2.10 | 85.50 | 28.60 | 128.30 | 1.11 |
| Jean | 11.21 | 7.30 | 4.40 | 82.40 | 40.20 | 132.80 | 1.54 |
| Simon | | | 6.10 | 96.20 | 45.30 | 155.50 | |
| MEAN | 9.98 | 8.08 | 4.93 | 72.64 | 37.91 | 123.39 | 1.45 |
| STD | 2.85 | 3.46 | 1.90 | 17.21 | 5.98 | 16.53 | 0.63 |

TABLE 20

CORN: FEMALES

| SAMPLES Name | Campest mg/dl | sitoste mg/dl | FSR pools/d | LDL mg/dl | HDL mg/dl | Tot. chol mg/dl | camp/sit |
|---|---|---|---|---|---|---|---|
| Elizabeth | 9.30 | 11.50 | | 55.8 | 49.70 | 116.10 | 0.81 |
| Mary | 18.40 | 21.50 | | 97.4 | 57.60 | 136.30 | 0.88 |
| Paula | 6.70 | 7.00 | | 84 | 34.40 | 135.30 | 0.96 |
| Stepbanie | 4.40 | 10.00 | | 45.5 | 44.80 | 106.90 | 0.44 |
| Manon | | | 8.50 | 74.10 | 36.70 | 119.80 | |
| MEAN | 9.70 | 12.50 | 8.50 | 71.36 | 44.54 | 122.88 | 0.77 |
| STD | 5.31 | $ .44 | 0.00 | 18.74 | 8.50 | 11.36 | 0.20 |

Discussion

In humans, two common patterns of lipoprotein cholesterol and triglycerides are known. The female pattern spans across reproductive years and consists of relatively low TC* and LDL-Ch ("bad" cholesterol") and high HDL-Ch* ("good" cholesterol) with high TG**.

The typical male pattern has relatively higher TC and LDL-Ch and lower HDL-Ch and TG. Not only did the Forbes' composition reverse the male pattern and enhance female cholesterol patterns (TC, LDL-Ch, HDL-CH) but also decreased female TG excess considered to be a risk factor for atherosclerosis and modified undesirable olive oil dietary effect on blood cholesterol. These are very significant and unexpected results.

The trial results are summarized in Table 21.

TABLE 21

Normocholesterolemic Subjects On Average Western Diet With Added Olive Oil, Olive Oil and Forbes FCP-3P1 Composition, Olive Oil and Soybean Plant Sterol Composition (Nulife)

| | Male | | | | Female | | | |
|---|---|---|---|---|---|---|---|---|
| | Relative changes in % with olive oil diet as a baseline (100.0%) | | | | | | | |
| Diet | TC | LDL-C | HDL-C | TG | UC | LDL-C | HDL-C | TG |
| Olive Oil* | 100% | 100% | 100% | 100% | 100% | 100% | 100% | 100% |
| Olive Oil + Forbes | 92.8% | 83.0% | 108.3% | 105.8% | 92.6% | 90.9% | 103.2% | 74% |
| Olive Oil + Nulife | 97.9% | 94.5% | 101.5% | 108.2% | 100.9% | 100.6% | 103.6% | 94.3% |

(Expressed as an average percent deviation from olive oil diet baseline)
TC* - Total Cholesterol
LDL-Ch** - Low Density Lipoprotein Cholesterol
HDL-Ch*** - High Density Lipoprotein Cholesterol
TG**** - Triglycerides Discussion The results of this study indicate that consumption of Forbes phytosterol mixture significantly reduces plasma total and LDL cholesterol levels with respect to olive oil. LDL cholesterol levels were also significantly lowered in the Forbes group with respect to the Nulife phytosterol group. A compensatory increase in fractional cholesterol synthetic rate was observed in the Forbes phytosterol group. This increased bisynthesis of cholesterol likely followed the reduction in plasma cholesterol levels through intestinal cholesterol losses.

There is significantly less absorption of phytosterols into the bloodstream in the Forbes phytosterol group versus the other treatment groups. Moreover, sitostanol was nondetectable in subjects' plasma, regardless of the phytosterol mixture consumed.

It is believed that sitostanol inhibits the absorption of phytosterols as well as cholesterol into the bloodstream. The olive treatment group served as a control for the Forbes and Nulife treatment groups—in that all variables were constant except for the additional of the respective phytosterol mixtures. The fact that total and LDL cholesterol values were greatly reduced in the Forbes group as opposed to the Nulife group, without a corresponding increase in plasma sitosterol concentrations, suggests that the sitostanol inhibits both cholesterol and its own absorption more than any of the Nulife component phytosterols. There remains the possibility that it is an interactive effect of different phytosterols mixed together in different proportions rather than the effect of an individual component which is influencing cholesterol metabolism. However, this possibility seems unlikely given that the effects of pure sitostanol versus Forbes phytosterol mixture was tested in hamsters and total and LDL cholesterol levels were lower in the former group (unpublished results). Curiously, the HDL cholesterol levels in the sitostanol group were lower than those for the Forbes group. Possibly, sitostanol is the more "active" ingredient in terms of cholesterol metabolism modification, but its action is enhanced by the presence of other phytosterols in the Forbes mixture.

It is interesting to note that although B-sitosterol is a main constituent of the Forbes phytosterol mixture, it is campesterol that is more concentrated in the plasma. It is possible that the presence of sitostanol selectively inhibits the absorption or facilitates the elimination of sitosterol relative to campesterol. It is speculated that this action may act as a secondary effect concurrent to the inhibition of cholesterol absorption.

While the results indicate that sitostanol is more effective than campesterol and sitosterol in terms of modifying cholesterol absorption into the bloodstream, this increase coincides with an increase in fractional synthetic rate. The net hypocholesterolemic effect of phytosterols is likely the result of an inhibition in cholesterol absorption or altered cholesterol synthesis and excretion. Phytosterols may thus displace cholesterol from mixed micelles during fat absorption, resulting in a reduction in the absorption rate of intestinal cholesterol. It is yet unknown whether phytosterols exert their influence in the gut lumen by trapping cholesterol or in the intestinal mucosa by interfering with the assembly and secretion of chylomicrons into the blood.

A favourable response to the administration of the Forbes composition has been demonstrated across virtually the entire lipid and lipoprotein profile both in male and female.

The low plasma HDL-Ch is regarded both in male and female as a cardiovascular risk factor. The individuals with high HDL-Ch have lower risk of coronary heart disease than individuals with low HDL-Ch even in the presence of other risk factors such as high LDL-Ch. Thus, a high HDL-Ch:LDL-Ch ratio can be considered a "negative' cardiovascular risk factor.

Table 22 provides evidence of a significant increase of 30.3% of male HDL-Ch:LDL-Ch ratio in olive oil-Forbes enriched diet approaching female HDL-Ch:LDL-Ch ratio,

TABLE 22

| | HDL/LDL Ratio* | | |
|---|---|---|---|
| Diet | Olive Oil | Olive Oil + Forbes | Olive Oil + Nulife |
| Male | 0.483 | 0.632 | 0.519 |
| Female | 0.609 | 0.695 | 0.627 |

*the higher the ratio the lesser the risk of atherosclerosis

Example 2

Human Study—Gender Profiles

The metabolic studies of Example 1 indicate that in men, saturated fat may be linked to atherosclerosis by an incur in intestinal absorption of more hydrophobic sterols (cholesterol and B-sitosterol) through an increase of bioavailability (solubility). Oils low in plant sterol content (olive oil) increase B-sitosterol and cholesterol absorption by high saturated and monounsaturated fatty acid content (Table 23). Vegetable oils with high plant sterol content and polyunsaturated fatty acids (come oil) modify plant sterol absorption by increasing less hydrophobic sterol (campesterol) intestinal absorption.

TABLE 23

|  | B-sitosterol | Campesterol | Sitostanol | Campesterol/ B-sitosterol Ratio |
|---|---|---|---|---|
| Nu-Life | 54.5% | 33.2% | • | 1.64 |
| FCP-3P1 (Forbes) | 51.7% | 18.3% | 21.4% | 2.8 |
| Olive Oil | 49.7% | • | • | • |

• Not detectable by GLC analysis

TABLE 25

HDL/LDL; CAMPESTEROL/B-sitOSTEROL CORRELATION*

| Males | | | | Females | | | |
|---|---|---|---|---|---|---|---|
| Olive Oil | Forbes FCP-3P1 | Nu-Life | Corn Oil | Olive Oil | Forbes FCP-3P1 | Nu-Life | Corn Oil |
| ↓↓ | ↑↑↑ | ↓ | ↓ | ↓ | ↑ | ↓ | ↑ |

↑ Positive Correlation, ↓ Negative Correlation
*Relative to Forbes FCP-3P1

Consequently, in men, a high campesterol/B-sitosterol ratio is an independent negative cardiovascular risk marker and can be used to monitor FCP-3P1 compliance and its efficacy independently of cholesterol (Table 26). The low campesterol/B-sitosterol ratio indicates high cardiovascular risk. Table 25 illustrates the positive correlation between HDL/LDL and campesterol/B-sitosterol ratios in both female and male subjects consuming FCP-3P1 enriched diet.

TABLE 26

PLANT STEROLS AS A MARKER OF CARDIOVASCULAR RISK

| DIET | Plasma Campesterol mg/dl | | Plasma B-sitosterol mg/dl | | Campesterol/ B-sitoerol Ratio | | Plant Sterols Male/Female Ratio | |
|---|---|---|---|---|---|---|---|---|
|  | Male | Female | Male | Female | Male | Female | Campesterol | B-sitosterol |
| Olive Oil | 4.4 | 7.8 | 6.0 | 8.0 | 0.73 | 0.97 | 0.56 | 0.75 |
| Forbes FCP-3P1 | 1.3 | 2.2 | 0.8 | 0.2 | 1.62 | 10.0 | 0.59 | 4.00 |
| Plant Sterols | 5.0 | 10.4 | 6.6 | 12.0 | 0.76 | 0.86 | 0.48 | 0.55 |
| Corn Oil | 9.9 | 9.7 | 7.0 | 12.5 | 1.4 | 0.78 | 1.02 | 0.56 |

Figure 14:
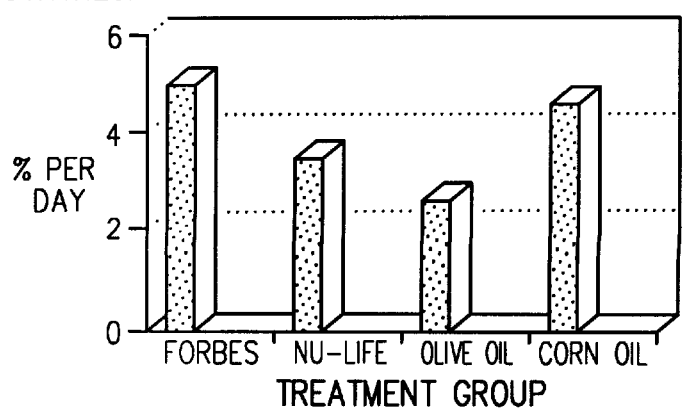
FIG. 14 is a graph depicting the synthesis of free cholesterol in red blood cells in the nervous treatment groups.

The effect of dietary oils and plant sterols is gender specific and modifiable by dietary plant sterol and fatty acid composition. In males, an increase in plasma cholesterol and in females an increase in plasma triglycerides are the result of a diet high in saturated fat. This effect is significantly modified in both genders by the composition of the present invention (FCP-3P1 or "Forbes") and corn oil rich in polyunsaturated fatty acids (FIG. 14). Consequently, a diet rich in saturated fat does not pose a cardiovascular risk and the atherogenicity of such a diet is codependant on other dietary constituents and gender. Commercial plant sterol extract did not normalize dietary saturated fatty acid effects indicating a co-effect between plant sterols and polyunsaturated fatty acids. Such an effect is seen in the corn oil experimental diet indicated by high plasma plant sterol levels.

In females, FCP-3P1 effects initially result in a significant decrease of plasma B-sitosterol and an increase of campesterol with high campesterol/B-sitosterol ratio, corresponding to a decrease in intestinal absorption of more hydrophobic sterols.

In males, the campesterol/B-sitosterol ratio increase is smaller indicating a shift in male sterol intestinal absorption towards more hydrophobic sterols. In experiments using male subjects, campesterol showed a positive correlation with HDL-cholesterol and cholesterol synthesis and a negative correlation with total cholesterol and LDL-cholesterol (Table II & III).

FCP-3P1's significant compensatory increase in hepatic cholesterol synthesis can be inhibited by statins. This clinically significant co-effect could be monitored by measuring changes in plasma campesterol/B-sitosterol ratio and could lead to significant total body cholesterol depletion.

Plasma plant sterol levels and campesterol/B-sitosterol ratio are significant indicators of diet habits and could serve as an important physiological diagnostic tool to follow efficacy of various treatment protocols, dietary compliance and helping practitioners assess other cardiovascular risks than cholesterol. Indeed campesterol plasma increase indicates a shift to normalization of total cholesterol, LDL-cholesterol, HDL-cholesterol and triglycerides, while B-sitosterol increase and/or reversal of campesterol/B-sitosterol ratio indicates high dietary cardiovascular risk in diet high in saturated fat and metabolic lipid disorders (Table 26 & 27).

TABLE 27

PLASMA LIPOPROTEIN AND PLANT STEROL CORRELATIONS

| Diet | | TC | LDL-C | HDL-C | TG | Campesterol | B-sitosterol |
|---|---|---|---|---|---|---|---|
| Olive Oil | $F^2$ | ↑ | ↑ | ↑→ | ↑↑↑ | ↑ | ↑ |
|  | $M^3$ | ↑↑ | ↑↑ | ↓→ |  | ↑ | ↑↑ |
| Plant Sterols | F | ↑↑ | ↑↑ | ↑→ | ↑↑ | ↑ | ↑↑ |
|  | M | ↑↑ | ↑↑ | ↑→ | ↑↑ | ↑ | ↑↑ |
| FCP-3P1 + Olive Oil | F | ↓ | ↓ | ↑ | ↓↓ | ↑↑ | ↓↓↓ |
|  | M | ↓ | ↓↓↓ | ↑↑ | ↑→ | ↑↑ | ↓↓ |

TABLE 27-continued

PLASMA LIPOPROTEIN AND PLANT STEROL CORRELATIONS

| Diet | | TC | LDL-C | HDL-C | TG | Campesterol | B-sitosterol |
|---|---|---|---|---|---|---|---|
| Corn Oil | F | ↓↓ | ↓↓ | ↓→ | ↓↓ | ↑↑ | ↑↑↑ |
| | M | ↓↓ | ↓↓ | ↓↓ | ↓→ | ↑↑↑ | ↑↑ |

2. Female
3. Male
Olive Oil: Positive correlation with cholesterol increase and B-sitosterol (F & M)
Plant Sterols: Positive correlation with cholesterol increase and plant sterols (F & M)
FCP-3P1: Positive correlation with HDL/campesterol (F & M) and cholesterol synthesis
Corn Oil: Negative correlation with cholesterol, triglycerides and campesterol in male and B-sitosterol in females.

Plasma campesterol represents a less abundant, more hydrophillic dietary plant sterol and in men is negatively associated with cholesterol absorption and cardiovascular risk. Dietary, more abundant plasma B-sitosterol represents, a more hydrophobic plant sterol and is positively associated with cholesterol absorption. Fatty acids have an important co-effect with plant sterols. An olive oil diet low in dietary plant sterol content results in relatively high plasma sterol levels. The plasma ratio of campesterol/B-sitosterol is relatively constant in spite of olive oil's low campesterol content. The increase of dietary plant sterols results in higher plasma plant sterol levels but the campesterol/B-sitosterol ratio remains relatively constant with little effect on the lipid profile. Monounsaturated and saturated fatty acids increase intestinal sterol absorption of more hydrophobic sterols and have a co-effect with
B-sitosterol and cholesterol. In males, the oils rich in plant sterols and polyunsaturated fatty acids have a co-effect with campesterol. Oils rich in polyunsaturated fatty acids in women decrease triglycerides as does the FCP-3P1 mixture. These findings have a significant implication on the atherogenicity of western diet.

Forbes research indicates that the diet has important effect on cholesterol metabolism leading to both qualitative and quantitative changes in both genders' lipid profiles.

FCP-3P1 improves both female and male lipid profiles in both quantitative and qualitative aspects and this effect is independent of dietary composition allowing liberal use of saturated fat (Table 28).

Discussion

In humans, two common patterns of lipoprotein cholesterol and triglycerides are known. The female pattern spans across reproductive years and consists of relatively low TC and LDL-Ch ("bad" cholesterol) and high HDL-Ch ("good" cholesterol) with high TG. The typical male pattern has relatively higher TC and LDL-Ch and lower HDL-Ch and TG. Not only did the Forbes' PCP-3P1 reverse the male pattern and enhanced female cholesterol pasterns (TC, LDL-CB, HDL-Ch) but also decreased female TG excess considered to be a risk factor for atherosclerosis and modified undesirable olive oil dietary effect on blood cholesterol.

Thus, a favourable response to FCP-3P1 administration has been demonstrated across virtually the entire lipid and lipoprotein profile in both male and female.

The low plasma HDL-Ch is regarded both in male and female as a cardiovascular risk factor. The individuals with high HDL-Ch have lower risk of coronary heart disease than individuals with low HDL-Ch even in the presence of other risk factors such as high LDL-Ch. Thus, a high HDL-Ch:LDL-Ch ratio can be considered a "negative" cardiovascular risk factor, Table 22 (above) provides evidence at significant increase of 30.3% of male HDL-Ch:LDL-Ch ratio in olive oil Forbes FCP-3P1 enriched diet approaching female HDL-Ch:LDL-Ch ratio.

This was a short term low dose study. The human trials conducted with plant sterols usually required several months to achieve the full therapeutic effect. Common plant sterols, high in vegetarian diets, exhibit a solid safety record having been in experimental and clinical use for over 50 years.

On an average western diet high in saturated fat and cholesterol, FCP-3P1 inhibits both cholesterol and B-sitosterol absorption "unmasking" campestanol gender differences, with campesterol plasma levels being higher in females, presumably due to faster female enterohepatic campesterol cycle, causing inhibition of B-sitosterol plasma excretion by hepatocytes. In males, this shift is not as apparent because of a shift of intestinal sterol absorption to more hydrophobic B-sitosterol. This shift in male absorption sterol pattern is reversed to the female absorption pattern by FCP-3P1.

Forbes dietary metabolic studies indicate two general dietary patterns:

Type I (Southern or Mediterranean Pattern)

Consists of high dietary monounsaturated and saturated fatty acids and low dietary plant sterols, polyunsaturated

TABLE 28

NORMOCROLESTEROLEMIC SUBJECTS ON AVERAGE WESTERN DIET* WITH ADDED OLIVE OIL, OLIVE OIL AND FORBES FCP-3P1 COMPOSITION, OLIVE OIL SOYBEAN PLANT STEROL COMPOSITION (NU-LIFE)

| | Male | | | | Female | | | |
|---|---|---|---|---|---|---|---|---|
| | Relative changes in % with olive oil diet as a baseline (100.0%) | | | | | | | |
| Diet | TC | LDL-C | HDL-C | TG | UC | LDL-C | HDL-C | TG |
| Olive Oil* | 100% | 100% | 100% | 100% | 100% | 100% | 100% | 100% |
| Olive Oil + Forbes | 92.8% | 83.0% | 108.3% | 105.8% | 92.6% | 90.0% | 103.2% | 74% |
| Olive Oil + Nulife | 97.9% | 94.5% | 101.5% | 108.2% | 100.9% | 100.6% | 103.6% | 94.3% |

Expressed as an average percent deviation from olive oil diet baseline
*Dietary cholesterol 350 mg–400 mg
TC - Total Cholesterol
LDL-Ch - Low Density Lipoprotein Cholesterol
HDL-Ch - High Density Lipoprotein Cholesterol
TG - Triglycerides fatty acids and cholesterol content. The overall cholesterol metabolism tends to preserve endogenous (internal) cholesterol resources by limiting enterohepatic cholesterol loss.

The population has high HDL cholesterol reflecting an increase in tissues demand for cholesterol and lower TC and LDL-cholesterol. The diet CVR risk is low but under adverse metabolic dietary conditions, the diet can be atherogenic.

Type II (Northern or Western Pattern)

Consists of high dietary saturated and poly unsaturated fatty acids and high plant sterols and cholesterol content. The overall cholesterol metabolism tends to eliminate excess cholesterol by an increase in enterohepatic cholesterol pool losses. The population has low HDL, high TC and LDL-C reflecting a decrease in tissue demand for cholesterol. The diet CVR factor is higher but under adverse dietary metabolic conditions can vary.

The study of FCP-3P1 plant sterol composition effect on cholesterol metabolism in normocholesterolemic subjects consuming average western diet under controlled laboratory conditions let to the discovery of two gender specific metabolic patterns.

A. Female Pattern

Associated with relatively low TC and LDL cholesterol and high HDL cholesterol and high triglycerides. The dietary marker of female pattern is campesterol. The ratio of campesterol and B-sitosterol is high.

B. Male Pattern

Associated with high TC and LDL cholesterol and low HDL cholesterol and low TG. The dietary marker of male pattern is B-sitosterol. The ratio of campesterol and B-sitosterol is low.

C. Lipid Disorder

Patients have very low campesterol/B-sitosterol ratio.

In both Type I and Type II diet and both genders, an important co-effect between dietary constituents takes place.

I Co-effect between saturated fatty acids and cholesterol absorption in cholesterol pool Type I diet in both females and males.

II Co-effect between plant sterols and polyunsaturated fatty acids in males and females.

a) Female Co-effect

Improvement in cholesterol profile indicating co-effect of dietary fatty acids and campesterol with estrogen on cholesterol enterocyte transport.

b) Male Co-Effect

Inhibiting male hormone effect on cholesterol enterocyte absorption by decrease of B-sitosterol and cholesterol and increased campesterol absorption.

Example 3

Rabbit Study

The following example examines the effect of plant sterols derived from soybean, the composition of the present invention (Forbes) or pure sitostanol on plasma lecithin-cholesterol acetyl transferase ("LCAT") activity and on free cholesterol esterification rate in New Zealand White (NZW) male rabbits fed 0.5% cholesterol for 65 days.

Methods

Twenty four NZW rabbits weighing 1.6 to 1.8 Kg were divided into four groups of n=6. They were accommodated for two weeks in the animal care facility at McGill University prior to a 65 days feeding period of semi-purified diet. All groups received 0.5% cholesterol in their diet in addition to one of three mixture of plant sterols for the non control groups: soybean (65% β-sitosterol, 20% campesterol and 15% dihydrobrassicasterol), Forbes as per one of the embodiments of the present invention (65% β-sitosterol, 16% campesterol and 17% sitostanol) and sitostanol (89% purity with traces of long chain fatty acyls and campestanol). Food intake was measured every three days, and body weight every one week during the study period.

LCAT activity and plasma cholesterol esterication rate were accomplished in Ste Paul's hospital at the ASL facility in Vancouver (Dr. Frholich's lab). For detailed procedures refer to Dr. Pritchard, ASL director. Briefly, 30 pl of labeled $H^3$ cholesterol in ethanolosomes with 10 pl of apoA-1 and 85 pl of assay buffer were mixed together, incubated for 30 min at 37° C., then added to 15 pl plasma sample in a glass culter tube to which 60 pl of BSA/β-mercaptoethanol was added. The sample-mixture was incubated for 30 min at 37° C. The enzymatic reaction was stopped with 1 ml of 99% ethanol. Assay samples were incubated for 1 h at 60° C., centrifuged for 10 min at 3000 rpm (1710×g), then transferred to clean glass tubes and dried under nitrogen at 60° C. An internal standard of free cholesterol and ester-cholesterol was added to each sample. The lipid extracts were resuspended in 50 pl chloroform and streaked on pre-coated TLC plastic sheets silica gels 60 $F_{254}$ (E. Merck). The plates were developed in a glass tank containing and saturating with petroleum ether, diethyl ether and acetic acid (105:18:1.5, V:V:V) for 8–10 min. Unesterified cholesterol and cholesterol ester bands were visualized with iodine, transferred to 5 ml scintillation vials. Toluene containing omnifluor (4 g/l) was added to each vial and then left for 1 h before reading. Cholesterol esterification rate (PER) was measured after equilibration and labelling of internal free cholesterol for 24 h with $^3H$-cholesterol. The procedures applied in measuring esterified cholesterol are similar to the previous ones.

Results

Food intake among different groups did not show significant variations. Rabbit's daily food intake ranged between 54.6 to 87.8 g. The rabbits' daily chow consumption during the accommodation period was around 100 g.

LCAT activity and cholesterol esterification rate

Figure 8:
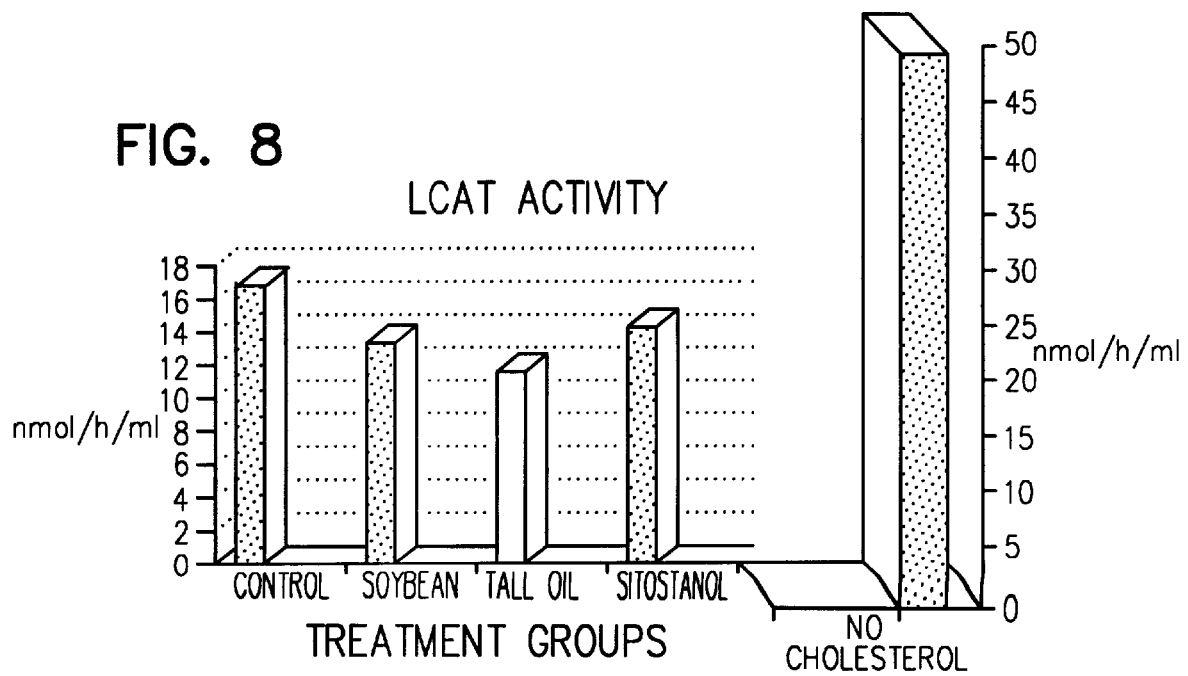
FIG. 8 is a graph representing the level of LCAT enzyme activity as teen various treatment groups.
Figure 9:
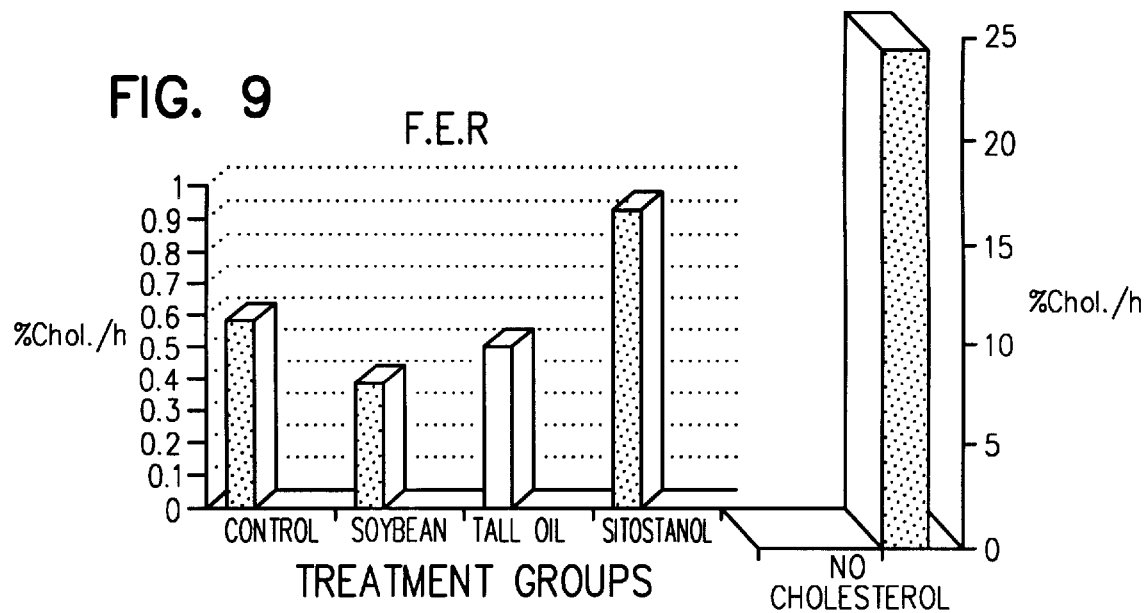
FIG. 9 is a graph representing the F.E.R. values of each of the treatment groups.
Figure 10:
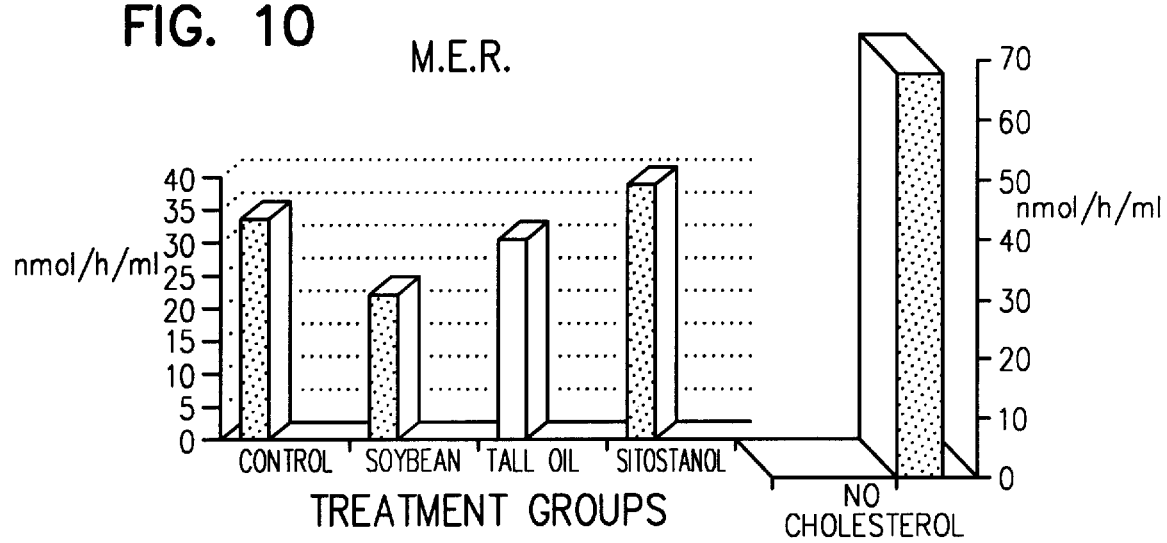
FIG. 10 is a graph representing the M.E.R. profile of each of the treatment groups.

The results obtained showed a decrease in LCAT activity by 31.1% in the Forbes fed group as compared to the control one; mean values are 11.58±2.06 and 16.81±5.34 nmol/h/ml respectively. However, the mean of the values were not significant, P=0.16 (FIG. 8). LCAT activity from human control showed a value of 28.86 nmol/h/ml which a rabbit LCAT activity gave a value of 49.44 nmol/h/ml. Both values are considered with in the expected normal range. FER values were the lowest in the soybean and tall oil groups; the means were 0.496±0.2 and 0.82±0.19%/h respectively. The mean activity was significantly different as compared to the sitostanol group, P=0.014 (FIG. 9). Mean plasma cholesterol esterification rate was the highest in the sitostanol treated group with soybean being the lowest; both groups were significantly different, P<0.05 (FIG. 10). The ratio of unesterified esterified cholesterol ranged between 24 to 42%. No difference in the mean values was observed among the different groups.

LCAT activity was the lowest in the Forbes treated group. LCAT activity in normal rabbits (no cholesterol or phytosterol fed rabbits) was >168% higher than any of the four cholesterol groups. The first explanation could be that the enzyme content was a limiting factor in the assay. That is, with extremely high lipidimic rabbits (200 to 577 mg/dl unesterified cholesterol (UC)), LCAT would esterify a certain concentration of endogenous and exogenous UC (30 wg) but not all the UC available. LCAT will be depleted before esterifying all the endogenous and exogenous UC. Another possible explanation is that a high plasma cholesterol levels, lipoproteins are aggregated in bigger particles which become less accessible to LCAT enzyme. This factor will explain the low activity observed, but it will not explain why the Forbes group had lower activity than the other three groups. Sitostanol treated group showed similar LCAT activity as the control group, while that of soybean was lower and Forbes the lowest. Sitostanol has the lowest absorption rate as compared to the other two plant sterol groups which suggests that sitostanol did not exhibit any internal effect on the LCAT enzyme while the more absorbed phytosterols showed a certain effect on LCAT activity. FER values were the highest in the sitostanol group which showed the lowest cholesterol concentration. It correlates with the high LCAT activity in the same group suggesting that at this total cholesterol concentration (635 mg/dl). LCAT was not down regulated with cholesterol.

In summary, blood cholesterol esterification leads to an increase in cholesterol atherogenicity. In this rabbit study, one of the compositions of the present invention resulted in a 31.1% LCAT activity decrease. The total serum phytosterol-cholesterol ratio was 2:1 indicating an "intrinsic" effect and confirming the dual phytosterol effect described herein.

We claim:

1. A method of assessing in a subject animal a risk for cardiovascular disease or a related disorder, comprising:
   obtaining a serum sample from the subject animal;
   determining a campesterol level in the serum sample;
   determining a beta-sitosterol level in the serum sample;
   dividing the campesterol level by the beta-sitosterol level to determine a campesterol/beta-sitosterol ratio;
   comparing said campesterol/beta-sitosterol ratio with a campesterol/beta-sitosterol ratio determined for a serum sample obtained from a normal control animal; and
   correlating a low campesterol/beta-sitosterol ratio for the serum sample from the subject animal as compared to the campesterol/beta-sitosterol ratio for the serum sample from the normal control animal with the risk for cardiovascular disease or a related disorder.

2. The method of claim 1 wherein the campesterol/beta-sitosterol ratio in the serum sample of the normal control animal is not less than 0.75.

3. The method of claim 1 wherein the campesterol/beta-sitosterol ratio in the serum sample of the normal control animal is between 1.0 and 1.5.

4. The method of claim 1 wherein the subject animal is human.

5. The method of claim 1 further comprising selecting the serum campesterol level as an indicator and correlating the level to a rate of cholesterol synthesis and a level of serum high-density lipoprotein cholesterol in the subject animal.

6. A method of assessing in a subject animal a risk of cardiovascular disease and lipid disorders comprising:
   determining in the subject animal a ratio of serum campesterol to beta-sitosterol;
   determining in the subject animal a level of serum total phytosterol;
   determining in the subject animal a level of serum total cholesterol;
   comparing said ratio of serum campesterol to beta-sitosterol, said level of serum total phytosterol and said level of serum total cholesterol so determined to a respective ratio of serum campesterol to beta-sitosterol, level of serum total phytosterol and level of serum total cholesterol determined for a serum sample from a normal control animal; and
   correlating a low campesterol/beta-sitosterol ratio, a high serum total phytosterol level and a high serum total cholesterol level for the serum sample from the subject animal as compared to the campesterol/beta-sitosterol ratio, the serum total phytosterol level and the serum total cholesterol level for the serum sample from the normal control animal with the risk for cardiovascular disease and lipid disorders.

7. The method of claim 6 wherein the ratio of serum campesterol to beta-sitosterol in the normal control animal is not less than 0.75.

8. The method of claim 6 wherein the ratio of serum campesterol to beta-sitosterol in the normal control animal is between 1.0 and 1.5.

9. The method of claim 6 wherein the level of serum total cholesterol in the normal control animal is not more than 5.2 mmole/L.

10. The method of claim 6 wherein the level of serum total cholesterol in the normal control animal is from about 2.0 to 6.0 $\mu$mole/L.

11. The method of claim 6 wherein the subject animal is human.

12. A method of assessing in a subject animal a risk for cardiovascular disease and a related disorder comprising determining in said subject animal a level of serum total phytosterol and a level of serum total cholesterol and comparing said levels to respective levels in serum of a normal control animal wherein:
   a high serum total phytosterol level and low serum total cholesterol level as compared to said levels in the normal control animal indicates a subject animal not requiring therapeutic or dietary intervention;
   a high serum total phytosterol level and high serum total cholesterol level as compared to said levels in the normal control animal indicates a subject animal at risk for lipid metabolic disorders;
   a low serum total phytosterol level and low serum total cholesterol level as compared to said levels in the normal control animal indicates a subject animal at risk for diabetes or hypothyroidism; and
   a low serum total phytosterol level and high serum total cholesterol level as compared to said levels in the normal control animal indicates an animal at risk for cardiovascular disease.

13. The method of claim 12 further comprising formulating a suitable intervention protocol by determining in the subject animal a ratio of serum campesterol to serum beta-sitosterol and comparing said ratio to a ratio of serum campesterol to serum beta-sitosterol obtained for a normal control animal wherein the ratio for the normal control animal is not less than 1.0, wherein:
   a high ratio of serum campesterol to serum beta-sitosterol and a high serum total phytosterol level and low serum total cholesterol level as compared to said ratio and said levels in the normal control animal indicates a subject animal not requiring further intervention;
   a low ratio of serum campesterol to serum beta-sitosterol and a high serum total phytosterol level and high serum total cholesterol level as compared to said ratio and said levels in the normal control animal indicates a subject animal in need of treatment to increase said serum total phytosterol level and said ratio of serum campesterol to serum beta-sitosterol; and a low ratio of serum campesterol to serum beta-sitosterol and a low serum total phytosterol level and a low serum total phytosterol/serum total cholesterol ratio as compared to the same ratios and level in the normal control animal indicates a subject animal requiring treatment for either diabetes or thyroid disease or in need of dietary modification to increase the serum total phytosterol level and the ratio of serum campesterol to serum beta-sitosterol.

* * * * *